US005614389A

United States Patent [19]
Auerbach

[11] Patent Number: 5,614,389
[45] Date of Patent: *Mar. 25, 1997

[54] METHODS FOR THE ISOTHERMAL AMPLIFICATION OF NUCLEIC ACID MOLECULES

[75] Inventor: Jeffrey I. Auerbach, Rockville, Md.

[73] Assignee: Replicon, Inc., Rockville, Md.

[ * ] Notice: The term of this patent shall not extend beyond the expiration date of Pat. No. 5,354,668.

[21] Appl. No.: 533,852

[22] Filed: Sep. 26, 1995

Related U.S. Application Data

[63] Continuation-in-part of Ser. No. 383,327, Feb. 3, 1995, which is a continuation of Ser. No. 136,405, Oct. 15, 1993, Pat. No. 5,354,668, which is a continuation-in-part of Ser. No. 933,945, Aug. 24, 1992, abandoned, which is a continuation-in-part of Ser. No. 924,643, Aug. 4, 1992, abandoned.

[51] Int. Cl.$^6$ ........................................... C12P 19/34
[52] U.S. Cl. .......................... 435/91.2; 435/6; 435/91.1
[58] Field of Search ........................ 435/6, 91.1, 91.2

[56] References Cited

U.S. PATENT DOCUMENTS

| 4,582,788 | 4/1986 | Erlich | 435/6 |
|---|---|---|---|
| 4,673,640 | 6/1987 | Backman | 435/68 |
| 4,683,194 | 7/1987 | Saiki et al. | 435/6 |
| 4,959,317 | 9/1990 | Sauer | 435/172.3 |
| 5,354,668 | 10/1994 | Auerbach | 435/91.1 |
| 6,683,202 | 7/1987 | Mullis | 435/91 |

FOREIGN PATENT DOCUMENTS

| 329822 | 8/1989 | European Pat. Off. . |
|---|---|---|
| WO88/10315 | 12/1988 | WIPO . |
| WO89/06700 | 7/1989 | WIPO . |
| WO90/11375 | 10/1990 | WIPO . |
| WO94/03624 | 2/1994 | WIPO . |

OTHER PUBLICATIONS

Mullis et al., "Specific Enzymatic Amplification of DNA in Vitro: The Polymerase Chain Reaction," *Cold Spring Harbor Symp. Quant. Biol.* 51:263–273 (1986).

Higuchi, "Using PCR to Engineer DNA, In: *PCR Technology*," Erlich, H. (ed.), Stockton Press, NY, 1989, pp. 61–68.

Hoess, R. et al., "The Nature of the Interaction of the P1 Recombinase Cre with the Recombining Site loxP," *Cold Spring Harbor. Symp. Quant. Biol.* 49:761–768 (1984).

Hamilton, D.L. et al., "Site–Specific Recombination by the Bacteriophage P1 loxP–Cre System," *J. Molec. Biol.* 178:481–486 (1984).

Sauer, B. "Functional Expression of the cre–lox Site–Specific Recombination System in the Yeast Saccharomyces cerevisiae," *Molec. Cell. Biol.* 7:2087–2096 (1987).

Sauer, B. et al. "Site–Specific DNA Recombination in Mammalian Cells by the Cre Recombinase of Bacteriophage P1," *Proc. Natl. Acad. Sci. (U.S.A.)* 85:5166–5170 (1988).

Abremski, K. et al., "Studies on the Properties of P1 Site–Specific Recombination: Evidence for Topologically Unlinked Products Following Recombination," *Cell* 32:1301–1311 (1983).

Hoess, R. et al., "P1 Site–Specific Recombination: Nucleotide Sequence of the Recombining Sites," *Proc. Natl. Acad. Sci. (U.S.A.)* 79:3398–3402 (1982).

Sternberg, N. et al., "Site–Specific Recombination and Its Role in the Life Cycle of Bacteriophage P1," *Cold Spring Harbor Symp. Quant. Biol.* 45:297–309 (1981).

Hoess, R. et al., "Interaction of the Bacteriophage P1 Recombinase Cre with the Recombining Site loxP," *Proc. Natl. Acad. Sci. (U.S.A.)* 81:1026–1029 (1984).

(List continued on next page.)

*Primary Examiner*—Kenneth R. Horlick
*Attorney, Agent, or Firm*—Jeffrey I. Auerbach

[57] ABSTRACT

Methods for amplifying a nucleic acid molecule which employs a single primer, and in which the amplification is performed under isothermal conditions. The invention also includes kits containing reagents for conducting the method.

20 Claims, 19 Drawing Sheets

OTHER PUBLICATIONS

Abremski, K. et al., "Bacteriophage P1 Site–Specific Recombination: Purification and Properties of the Cre Recombinase Protein," *J. Molec. Biol.* 259:1509–1514 (1984).

Abremski, K. et al., "Bacteriophage P1 Cre–loxP Site–Specific Recombination: Site–Specific DNA Topoisomerase Activity of the Cre Recombination Protein," *J. Biol. Chem.* 261:391–396 (1986).

Sauer, B. et al., "Site–Specific Insertion of DNA into a Pseudorabies Virus Vector," *Proc. Natl. Acad. Sci. (U.S.A.)* 84:9108–9112 (1987).

Palazzolo, M.J. et al., "Phage Lambda cDNA Cloning Vectors for Subtractive Hybridization, Fusion–Protein Synthesis and Cre–loxP Automatic Plasmid Subcloning," *Gene* 88:25–36 (1990).

Kwoh D. et al., "Transcription–Based Amplification System and Detection of Amplified Human Immunodeficiency Virus Type 1 with a Bead–Based Sandwich Hybridization Assay," *Proc. Natl. Acad. Sci. (U.S.A.)* 86:1173 (1989).

Ohara, O. et al., "One–Sided Polymerase Chain Reaction: The Amplification of cDNA," *Proc. Natl. Acad. Sci. (U.S.A.)* 86:5673–5677 (1989).

Frohman, M.A., "RACE: Rapid Analysis of cDNA Ends," In: *PCR Protocols: A Guide to Methods and Applications* Academic Press, NY (1990).

Wu, D.Y. et al., "The Ligation Amplification Reaction (LAR) — Amplification of Specific DNA Sequences Using Sequential Rounds of Template–Dependent Ligation," *Genomics* 4:560 (1989).

Mullis, K.B. et al., "Specifi Synthesis of DNA in Vitro via a Polymerase–Catalyzed Chain Reaction," In: *Met. Enzymol.* 155:335–350 (1987).

Walker, G.T. et al., "Isothermal in vitro Amplification of DNA by a Restriction Enzyme/DNA Polymerase System," *Proc. Natl. Acad. Sci. (U.S.A.)* 89:392–396 (1992).

Chatterjee, D.K. et al., "Cloning and Overexpression of the Gene Encoding Bacteriophage T5 DNA Polymerase," *Gene* 97:13–19 (1991).

Gillin, F. et al., "Control of Mutation frequency by Bacteriophage T4 DNA Polymerase: I. The CB120 Antimutator DNA Polymerase is Defective in Strand Displacement," *J. Biol. Chem* 251:5219–5224 (1976).

Kolodner, R. et al., "Gene 4 Protein of Bacteriophage T7: Characterization of the Product Synthesized by the T7 DNA Polymerase and Gene 4 Protein in the Absence of Ribonucleoside 5'–Triphosphates," *J. Biol. Chem* 253:574–584 (1978).

Eki, T. et al., "Influence of Poly(ADP–ribose) Polymerase on the Enzymatic Synthesis of SV40 DNA," *J. Biol. Chem* 266:3087–3100 (1991)

Parada, C. et al., "Transcriptional activation of pBR322 DNA can lead to Duplex DNA Unwinding Catalyzed by the *Escherichia coli* Preprimosome," *J. Biol. Chem* 264:15120–15129 (1989).

Dattagupta, N., "Nucleic Acid Amplification Employing Transcribable Hairpin Probe," *Chem. Abstr.* 115(10):107787g [citing European Patent Appln. 427074 A2 (15 May 1991)].

Bellofatto, V. et al., "Generation of a Tn5 Promoter Probe and Its Use in the Study of Gene Expression in *Caulobacter crescentus*," Proc. Natl. Acad. Sci. (U.S.A.) 81:1035–1039 (1984).

A

B

C

D or

MODIFICATION OF 5' TERMINUS

METHODS FOR THE ISOTHERMAL AMPLIFICATION OF NUCLEIC ACID MOLECULES

CROSS-REFERENCE TO RELATED APPLICATIONS

This application is a continuation-in-part of U.S. patent application Ser. No. 08/383,327 (filed Feb. 3, 1995), which is a continuation-in-part of PCT Application No. PCT/US93/07309 (filed Aug. 4, 1993), which is a continuation-in-part of U.S. patent application Ser. No. 07/933,945, filed Aug. 24, 1992 (which application was abandoned in favor of continuation application U.S. patent application Ser. No. 08/136,405, filed Oct. 15, 1993, which issued on Oct. 11, 1994 as U.S. Pat. No. 5,354,668, U.S. patent application Ser. No. 07/933,445, which is a continuation-in-part of U.S. patent application Ser. No. 07/924,643, filed Aug. 4, 1992 (now abandoned).

FIELD OF THE INVENTION

The present invention is in the field of recombinant DNA technology. This invention is directed to a process for amplifying a nucleic acid molecule, and to the molecules employed and produced through this process.

BACKGROUND OF THE INVENTION

Assays capable of detecting the presence of a particular nucleic acid molecule in a sample are of substantial importance in forensics, medicine, epidemiology and public health, and in the prediction and diagnosis of disease. Such assays can be used, for example, to identify the causal agent of an infectious disease, to predict the likelihood that an individual will suffer from a genetic disease, to determine the purity of drinking water or milk, or to identify tissue samples. The desire to increase the utility and applicability of such assays is often frustrated by assay sensitivity. Hence, it would be highly desirable to develop more sensitive detection assays.

The usefulness of a detection assay is often limited by the concentration at which a particular target nucleic acid molecule is present in a sample. Thus, methods that are capable of amplifying the concentration of a nucleic acid molecule have been developed as adjuncts to detection assays.

One method for overcoming the sensitivity limitation of nucleic acid concentration is to selectively amplify the nucleic acid molecule whose detection is desired prior to performing the assay. Recombinant DNA methodologies capable of amplifying purified nucleic acid fragments in vivo have long been recognized. Typically, such methodologies involve the introduction of the nucleic acid fragment into a DNA or RNA vector, the clonal amplification of the vector, and the recovery of the amplified nucleic acid fragment. Examples of such methodologies are provided by Cohen et al. (U.S. Pat. No. 4,237,224), Maniatis, T. et al., *Molecular Cloning (A Laboratory Manual)*, Cold Spring Harbor Laboratory, 1982, etc.

In many instances in clinical medicine and diagnostics, however, the concentration of a target species in a sample under evaluation is so low that it cannot be readily cloned. To address such situations, methods of in vitro nucleic acid amplification have been developed that employ template directed extension. In such methods, the nucleic acid molecule is used as a template for extension of a nucleic acid primer in a reaction catalyzed by polymerase.

One such template extension method is the "polymerase chain reaction" ("PCR"), which is among the most widely used methods of DNA amplification (Mullis, K. et al., *Cold Spring Harbor Symp. Quant. Biol.* 51:263–273 (1986); Erlich H. et al., EP 50,424; EP 84,796, EP 258,017, EP 237,362; Mullis, K., EP 201,184; Mullis K. et al., U.S. Pat. No. 4,683,202; Erlich, H., U.S. Pat. No. 4,582,788; Saiki, R. et al., U.S. Pat. No. 4,683,194 and Higuchi, R. "PCR Technology," Ehrlich, H. (ed.), Stockton Press, New York, 1989, pp 61–68), which references are incorporated herein by reference).

The polymerase chain reaction can be used to selectively increase the concentration of a nucleic acid molecule even when that molecule has not been previously purified and is present only in a single copy in a particular sample. The method can be used to amplify either single- or double-stranded DNA. The essence of the method involves the use of two oligonucleotides to serve as primers for the template-dependent, polymerase mediated replication of the desired nucleic acid molecule.

The precise nature of the two oligonucleotide primers of the PCR method is critical to the success of the method. As is well known, a molecule of DNA or RNA possesses directionality, which is conferred through the 5'→3' linkage of the sugar-phosphate backbone of the molecule. Two DNA or RNA molecules may be linked together through the formation of a phosphodiester bond between the terminal 5' phosphate group of one molecule and the terminal 3' hydroxyl group of the second molecule. Polymerase dependent amplification of a nucleic acid molecule proceeds by the addition of a nucleotide having 5' phosphate to the 3' hydroxyl end of a nucleic acid molecule. Thus, the action of a polymerase extends the 3' end of a nucleic acid molecule. These inherent properties are exploited in the selection of the two oligonucleotide primers of the PCR. The oligonucleotide sequences of the two primers of the PCR method are selected such that they contain sequences identical to, or complementary to, sequences which flank the sequence of the particular nucleic acid molecule whose amplification is desired. More specifically, the nucleotide sequence of the "first" primer is selected such that it is capable of hybridizing to an oligonucleotide sequence located 3' to the sequence of the desired nucleic acid molecule that is to be amplified, whereas the nucleotide sequence of the "second" primer is selected such that it contains a nucleotide sequence identical to one present 5' to the sequence of the desired nucleic acid molecule that is to be amplified. Both primers possess the 3' hydroxyl groups which are necessary for enzyme mediated nucleic acid synthesis.

In the polymerase chain reaction, the reaction conditions must be cycled between those conducive to hybridization and nucleic acid polymerization, and those which result in the denaturation of duplex molecules. In the first step of the reaction, the nucleic acid molecules of the sample are transiently heated, and then cooled, in order to denature any double stranded molecules that may be present. The "first" and "second" primers are then added to the sample at a concentration which greatly exceeds that of the desired nucleic acid molecule. When the sample is then incubated under conditions conducive to hybridization and polymerization, the "first" primer will hybridize to the nucleic acid molecule of the sample at a position 3' to the sequence of the desired molecule to be amplified. If the nucleic acid molecule of the sample was initially double stranded, the "second" primer will hybridize to the complementary strand of the nucleic acid molecule at a position 3' to the sequence of the desired molecule that is the complement of the sequence whose amplification is desired. Upon addition of a polymerase, the 3' ends of the "first" and (if the nucleic acid molecule was double stranded) "second" primers will be extended. The extension of the "first" primer will result in the synthesis of a DNA molecule having the exact sequence of the complement of the desired nucleic acid. Extension of the "second" primer will result in the synthesis of a DNA molecule having the exact sequence of the desired nucleic acid.

The PCR reaction is capable of exponentially amplifying the desired nucleic acid sequences, with a near doubling of the number of molecules having the desired sequence in each cycle. This exponential increase occurs because the extension product of the "first" primer contains a sequence which is complementary to a sequence of the "second" primer, and thus can serve as a template for the production of an extension product of the "second" primer. Similarly, the extension product of the "second" primer, of necessity, contain a sequence which is complementary to a sequence of the "first" primer, and thus can serve as a template for the production of an extension product of the "first" primer. Thus, by permitting cycles of hybridization, polymerization, and denaturation, an exponential increase in the concentration of the desired nucleic acid molecule can be achieved. Reviews of the polymerase chain reaction are provided by Mullis, K. B. (*Cold Spring Harbor Symp. Quant. Biol.* 51:263–273 (1986)); Saiki, R. K., et al. (*Bio/Technology* 3:1008–1012 (1985)); and Mullis, K. B., et al. (*Met. Enzymol.* 155:335–350 (1987), which references are incorporated herein by reference).

PCR technology is useful in that it can achieve the rapid and extensive amplification of a polynucleotide molecule. However, the method has several salient deficiencies. First, it requires the preparation of two different primers which hybridize to two oligonucleotide sequences of the target sequence flanking the region that is to be amplified. The concentration of the two primers can be rate limiting for the reaction. Although it is not essential that the concentration of the two primers be identical, a disparity between the concentrations of the two primers can greatly reduce the overall yield of the reaction.

A further disadvantage of the PCR reaction is that when two different primers are used, the reaction conditions chosen must be such that both primers "prime" with similar efficiency. Since the two primers necessarily have different sequences, this requirement can constrain the choice of primers and require considerable experimentation. Furthermore, if one tries to amplify two different sequences simultaneously using PCR (i.e. using two sets of two primers), the reaction conditions must be optimized for four different primers.

A further disadvantage of PCR is that it requires the thermocycling of the molecules being amplified. Since this thermocycling requirement denatures conventional polymerases, it thus requires the addition of new polymerase at the commencement of each cycle. The requirement for additional polymerase increases the expense of the reaction, and can be avoided only through the use of thermostable polymerases, such as Taq polymerase. Moreover, the thermocycling requirement attenuates the overall rate of amplification because further extension of a primer ceases when the sample is heated to denature double-stranded nucleic acid molecules. Thus, to the extent that the extension of any primer molecule has not been completed prior to the next heating step of the cycle, the rate of amplification is impaired.

Other known nucleic acid amplification procedures include transcription-based amplification systems (Kwoh D. et al., *Proc. Natl. Acad. Sci.* (U.S.A.) 86:1173 (1989); Gingeras T. R. et al., PCT appl. WO 88/10315 (priority: U.S. patent applications Ser. Nos. 064,141 and 202,978); Davey, C. et al., European Patent Application Publication no. 329, 822; Miller, H. I. et al., PCT appl. WO 89/06700 (priority: U.S. patent application Ser. No. 146,462, filed 21 Jan. 1988)), and "race" (Frohman, M. A., In: PCR Protocols: A Guide to Methods and Applications, Academic Press, New York (1990)) and "one-sided PCR" (Ohara, O. et al., *Proc. Natl. Acad. Sci.* (U.S.A.) 86:5673–5677 (1989)).

Methods based on ligation of two (or more) oligonucleotides in the presence of nucleic acid having the sequence of the resulting "dioligonucleotide", thereby amplifying the di-oligonucleotide, are also known (Wu, D. Y. et al., *Genomics* 4:560 (1989)).

An isothermal amplification method has been described in which a restriction endonuclease is used to achieve the amplification of target molecules that contain nucleotide 5'-[a-thio]triphosphates in one strand of a restriction site (Walker, G. T. et al., *Proc. Natl. Acad. Sci.* (U.S.A.) 89:392–396 (1992)).

All of the above amplification procedures depend on the principle that an end-product of a cycle is functionally identical to a starting material. Thus, by repeating cycles, the nucleic acid is amplified exponentially.

Methods that use thermocycling, e.g. PCR or Wu, D. Y. et al., *Genomics* 4:560 (1989)), have a theoretical maximum increase of product of 2-fold per cycle, because in each cycle a single product is made from each template. In practice, the increase is always lower than 2-fold. Further slowing the amplification is the time spent in changing the temperature. Also adding delay is the need to allow enough time in a cycle for all molecules to have finished a step. Molecules that finish a step quickly must "wait" for their slower counterparts to finish before proceeding to the next step in the cycle; to shorten the cycle time would lead to skipping of one cycle by the "slower" molecules, leading to a lower exponent of amplification.

SUMMARY OF THE INVENTION

The present invention concerns a method for achieving the amplification of a nucleic acid molecule using a single primer, under isothermal conditions.

In detail, the invention provides a method for amplifying a target polynucleotide region of a double-stranded nucleic acid molecule present in a sample, which comprises the steps:

(A) incubating linear double-stranded nucleic acid molecules in the presence of a polymerase, nucleotides, a Cre recombinase, a primer and a restriction endonuclease; wherein:
  (i) each of the linear double-stranded nucleic acid molecules has two ends and comprises:
    (a) a first lox site, located at a first end of the linear molecule;
    (b) a second lox site, located at a second end of the linear molecule, wherein the first and the second lox sites are oriented with respect to one another so as to permit the Cre to mediate the circularization of the linear double-stranded molecules, and to thereby form double-stranded circular molecules;
    (c) the target polynucleotide region, located internal to the first and second lox sites; and (d) a hemi-modified restriction site, located between the target polynucleotide region and one of the lox sites, wherein one strand of the hemi-modified restriction site of each of the linear molecules contains at least one modified nucleotide residue (especially of methylated nucleotides or (a-thio-)phosphorothioate nucleotides);

(ii) the restriction endonuclease is substantially incapable of cleaving a strand of a nucleic acid molecule that contains the modified nucleotide residue;

(iii) the primer comprises from 3' terminus to 5' terminus:

(a) a first polynucleotide region complementary to a 3' terminal portion of the target polynucleotide region;

(b) a second polynucleotide region containing at least one of the modified nucleotide residues (especially of methylated nucleotides or (a-thio-)phosphorothioate nucleotides), wherein, if the second polynucleotide region were hybridized to a complementary polynucleotide, a double-stranded polynucleotide would thereby be formed that would contain one or more restriction endonuclease cleavage sites that would be recognized by the restriction endonuclease; and (c) a third polynucleotide region, wherein, if the third polynucleotide region were hybridized to a complementary polynucleotide, a double-stranded polynucleotide would thereby be formed that would contain a lox site; and (iv) the incubation is conducted under conditions suitable for permitting:

(a) the Cre to circularize the linear double-stranded nucleic acid molecules and thereby form the double-stranded circular molecules;

(b) the restriction endonuclease to cleave one strand of the hemi-modified restriction endonuclease recognition site of the double-stranded circular molecule and thereby create an extendible 3' terminus;

(c) the polymerase and the nucleotides to mediate template dependent extension of the extendible 3' terminus and thereby cause displacement of a single-stranded polynucleotide containing the target polynucleotide region; the extension further resulting in the creation of a new hemi-modified restriction recognition site;

(d) the restriction endonuclease to cleave one strand of the newly created hemi-modified restriction endonuclease recognition site and thereby form a new extendible 3' terminus and permit the release of the single-stranded polynucleotide containing the target polynucleotide region; and (e) the primer to hybridize to the released single-stranded polynucleotide and to be extended by the polymerase and the nucleotides in a template-dependent extension to thereby form an additional copy of the linear double-stranded nucleic acid molecule;

(B) permitting: the Cre-directed circularization (A)(iv)(a) of the linear molecule, the creation of the extendible 3' terminus (A)(iv)(b), the template dependent extension (A)(iv)(c), the restriction endonuclease cleavage (A)(iv)(d), and the primer hybridization (A)(iv)(e), to occur, thereby amplifying the target polynucleotide region of the double-stranded nucleic acid molecule; and (C) maintaining the incubation conditions until a desired level of amplification of the target polynucleotide region of the double-stranded nucleic acid molecule has been attained.

The invention additionally concerns the embodiment of the above method wherein the linear double-stranded nucleic acid molecule recited in step (A) is obtained by primer extension of first primer molecules, the first primer molecules being nucleic acid molecules comprising from 3' terminus to 5' terminus:

(1) a first polynucleotide region complementary to a 3' terminal portion of the target polynucleotide region;

(2) a second polynucleotide region containing at least one modified nucleotide residue, wherein, if the second polynucleotide region were hybridized to a complementary polynucleotide, a double-stranded polynucleotide would thereby be formed that would contain one or more restriction endonuclease cleavage sites that would be recognized by a restriction endonuclease that is substantially incapable of cleaving a strand of a nucleic acid molecule that contains the modified nucleotide residue; and (3) a third polynucleotide region, wherein, if the third polynucleotide region were hybridized to a complementary polynucleotide, a double-stranded polynucleotide would thereby be formed that would contain a lox site.

The invention additionally concerns the embodiment of the above method wherein the linear double-stranded nucleic acid molecule recited in step (A) is obtained by a process comprising primer extension of second primer molecules, the second primer molecules and comprising from 3' terminus to 5' terminus:

(1) a first polynucleotide region having the sequence of a 5' terminal portion of the target polynucleotide;

(2) a second polynucleotide region, wherein, if the second polynucleotide region were hybridized to a complementary polynucleotide, a double-stranded polynucleotide would thereby be formed that would contain a lox site.

The invention additionally concerns the embodiment of the above method wherein the linear double-stranded nucleic acid molecule recited in step (A) is obtained by a process comprising ligating the target polynucleotide region into a restriction endonuclease recognition site of a linear nucleic acid molecule that contains a lox site at each end, the restriction endonuclease recognition site, and the hemi-modified restriction endonuclease recognition site.

The invention additionally concerns the embodiment of the above method wherein the linear double-stranded nucleic acid molecule recited in step (A) is obtained by a process comprising ligating the target polynucleotide region into a restriction endonuclease recognition site of a circular nucleic acid molecule that contains a lox site, the restriction endonuclease recognition site, and the hemi-modified restriction endonuclease recognition site.

The invention additionally provides a method for amplifying a target polynucleotide region of a double-stranded nucleic acid molecule present in a sample, the method comprising:

(A) incubating the sample under conditions sufficient to denature the double-stranded molecule and thereby form single-stranded nucleic acid molecules;

(B) incubating the formed single-stranded nucleic acid molecules in the presence of first primer molecules, the first primer molecules being single-stranded nucleic acid molecules, and comprising from 3' terminus to 5' terminus:

(1) a first polynucleotide region complementary to a 3' terminal portion of the target polynucleotide region;

(2) a second polynucleotide region containing at least one modified nucleotide residue (especially of methylated nucleotides or (a-thio)phosphorothioate nucleotides), wherein, if the second polynucleotide region were hybridized to a complementary polynucleotide, a double-stranded polynucleotide would thereby be formed that would contain one or more restriction endonuclease cleavage sites that would be recognized by a restriction endonuclease that is substantially incapable of cleaving a strand of a nucleic acid molecule that contains the modified nucleotide residue; and (3) a third polynucleotide region, wherein, if the third polynucleotide region were hybridized to a complementary polynucleotide, a double-stranded polynucleotide would thereby be formed that would contain a lox site;

wherein the incubation is conducted in the presence of a polymerase and nucleotides lacking the modification of the modified nucleotide residue of the first primer, the incubation being under conditions sufficient to (i) permit the first polynucleotide region of the first primer molecules to hybridize to the 3' terminus of the target polynucleotide, and (ii) permit template dependent extension of the first primer molecules, to thereby form first primer extension products;

(C) incubating the first primer extension products under conditions sufficient to denature double-stranded nucleic acid molecules and thereby produce unhybridized first primer extension products;

(D) incubating the unhybridized first primer extension products in the presence of second primer molecules, the second primer molecules being single-stranded nucleic acid molecules, and comprising from 3' terminus to 5' terminus:

(1) a first polynucleotide region having the sequence of a 5' terminal portion of the target polynucleotide; and (2) a second polynucleotide region, wherein, if the second polynucleotide region were hybridized to a complementary polynucleotide, a double-stranded polynucleotide would thereby be formed that would contain a lox site;

wherein the incubation is conducted in the presence of a polymerase and nucleotides lacking the modification of the modified nucleotides present in the first primer, the incubation being under conditions sufficient to permit (i) the unhybridized first primer extension products to hybridize to the 3' terminus of the second primer molecules, and (ii) template dependent extension of the first primer extension products, and of the second primer molecules, to thereby form linear double-stranded nucleic acid molecules having a lox site at each end, and containing the target polynucleotide that is to be amplified and a hemi-modified restriction site;

(E) incubating the linear double-stranded nucleic acid molecules of step (D)in the presence of Cre recombinase, the restriction endonuclease, the polymerase and the nucleotides lacking the modification of the modified nucleotides of the first primer; wherein the incubation permits the following reactions to occur:

(1) the Cre to circularize the linear double-stranded nucleic acid molecules having a lox site at each end, to thereby form a double-stranded circular molecule;

(2) the restriction endonuclease to cleave a non-modified nucleotide-containing strand of the hemi-modified restriction endonuclease recognition site of the double-stranded circular molecule to thereby form an extendible 3' terminus;

(3) the polymerase and the non-modified nucleotides to mediate template-dependent primer extension of the extendible 3' terminus to thereby cause displacement of a single-stranded polynucleotide containing the target polynucleotide region; the primer extension further resulting in the creation of a new hemi-modified restriction recognition site; and (4) the restriction endonuclease to cleave a non-modified nucleotide-containing strand of the newly created hemi-modified restriction endonuclease recognition site to thereby form a new extendible 3' terminus, and permit the release of the single-stranded polynucleotide containing the target polynucleotide region, wherein the displacement and the release accomplishes the desired amplification of the target polynucleotide; and (F) maintaining the incubation conditions of step (E) until a desired level of amplification of the target polynucleotide has been attained.

The invention additionally concerns the embodiments of the above methods wherein:

(1) the first primer molecules additionally contain a fourth polynucleotide region, the fourth polynucleotide region of the first primer molecules being located 5' to the third polynucleotide region of the first primer molecules, and having a nucleotide sequence complementary to at least a portion thereof, such that the third and fourth polynucleotide regions of the first primer molecules are hybridized to one another; and/or (2) the second primer molecules additionally contain a third polynucleotide region, the third polynucleotide region of the second primer molecules being located 5' to the second polynucleotide region of the second primer molecules, and having a nucleotide sequence complementary to at least a portion thereof, such that the second and third polynucleotide regions of the second primer molecules are hybridized to one another.

The invention additionally includes the embodiments of the above methods wherein the step (E) additionally permits the following reactions to occur:

(5) the first primer molecules to hybridize to the 3' terminus of the displaced and released single-stranded polynucleotides; and (6) the polymerase and the non-modified nucleotides to mediate the template-dependent extension of the hybridized first primer molecules, and of the hybridized displaced and released single-stranded polynucleotides, to thereby form linear double-stranded nucleic acid molecules having a lox site at each end, and containing the target polynucleotide region and a hemi-modified restriction site; the formed linear double-stranded molecules being substrates for the reaction (E)(1); and wherein the linear double-stranded nucleic acid molecules are permitted to become substrates of the reaction (E)(1).

The method particularly contemplates the embodiment wherein the first primer is provided in limiting amounts, such that the method amplifies one strand of the double-stranded nucleic acid target molecule to a greater extent than the other strand.

BRIEF DESCRIPTION OF THE FIGURES

FIG. 8A shows the twin origin "rolling circle" replicon that results from the extension of two primers during the amplification of a single-stranded circular molecule. FIG. 8B shows the Q and "rolling circle" replicons that result from the amplification of a double-stranded circular molecule.

DETAILED DESCRIPTION OF THE INVENTION

I. TERMINOLOGY OF THE INVENTION

Figure 1:
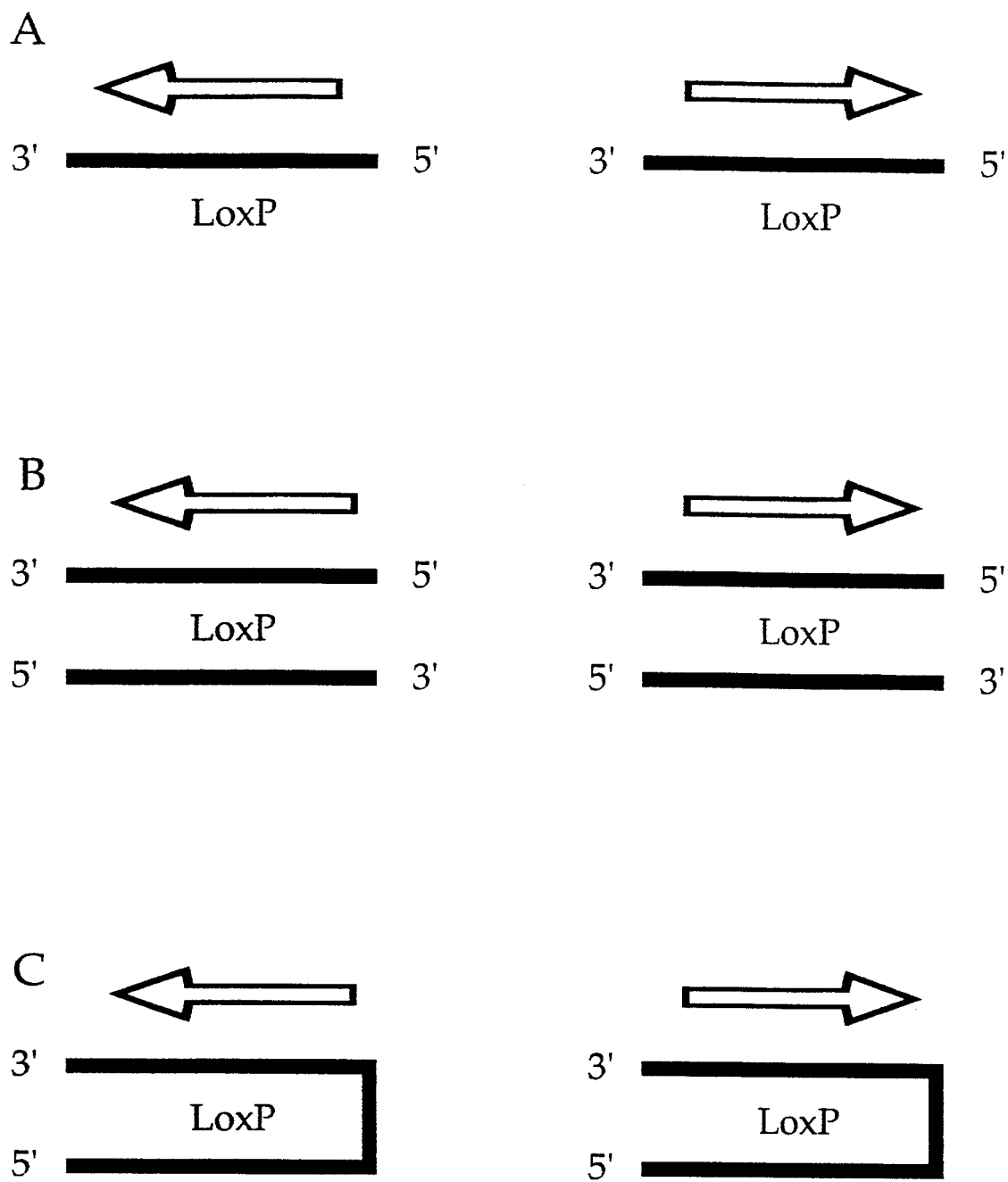
FIG. 1 (comprising Drawings A, B and C) shows examples of suitable 5' adaptor molecules.

The present invention provides a method for amplifying a "target" polynucleotide region of a nucleic acid molecule that is present in a sample. Such samples may include biological samples derived from a human or other animal source (such as, for example, blood, stool, sputum, mucus, serum, urine, saliva, teardrop, a biopsy sample, an histology tissue sample, a PAP smear, a mole, a wart, an agricultural product, waste water, drinking water, milk, processed foodstuff, air, etc.) including samples derived from a bacterial or viral preparation, as well as other samples (such as, for example, agricultural products, waste or drinking water, milk or other processed foodstuff, air, etc.).

As used herein, the term "desired" nucleic acid molecule is intended to refer to the nucleic acid molecule that is to be amplified by the present methods. The "desired" molecule can have been purified, or partially purified, or may be present in an unpurified state in the sample. A nucleic acid molecule that contains the "desired" molecule is said to be a "target" molecule. The nucleaic acid molecules of the present invention are described as "polynucleotides" in order to denote that they contain more than three nucleotide residues. The nucleic acid molecules of the present invention are further described as comprising "regions," in order to more fully describe the structural components of the molecules. The linear nucleic acid molecules of the invention contain terminal "portions." As used herein, such portions define a region at the end of the molecules.

As used herein, the term "amplification" refers to a "template-dependent process" that results in an increase in the concentration of a nucleic acid molecule relative to its initial concentration. As used herein, the term "template-dependent process" is intended to refer to a process that involves the template-dependent extension of a primer molecule. As such, the term amplification, as used herein, is intended to exclude in vivo vector-mediated propagation of the type described by Cohen et al. (U.S. Pat. No. 4,237,224); Maniatis, T. et al., (*Molecular Cloning A Laboratory Manual*, Cold Spring Harbor Laboratory, 1982), etc. The term "template dependent process" refers to nucleic acid synthesis of RNA or DNA wherein the sequence of the newly synthesized strand of nucleic acid is dictated by the well-known rules of complementary base pairing (see, for example, Watson, J. D. et al., In: *Molecular Biology of the Gene*, 4th Ed., W. A. Benjamin, Inc., Menlo Park, Calif. (1987)). As used herein, a sequence of one nucleic acid molecule is said to be the "complement" of another if it contains a T (or U), A, C, or G at a position in which the other molecule contains an A, T (or U), G or C, respectively.

The present invention employs a variety of different enzymes to accomplish the amplification of the desired nucleic acid molecule. A "polymerase" is an enzyme that is capable of incorporating nucleotides to extend a 3' hydroxyl terminus of a "primer molecule." A nucleotide that has been incorporated into a nucleic acid molecule is termed a nucleotide "residue." As used herein, a "primer" or "primer molecule" is a nucleic acid molecule, that when hybridized to a nucleic acid molecule, possesses a 3' hydroxyl terminus that can be extended by a polymerase. Polymerase enzymes are discussed in Watson, J. D. et al., In: *Molecular Biology of the Gene*, 4th Ed., W. A. Benjamin, Inc., Menlo Park, Calif. (1987), which reference is incorporated herein by reference, and similar texts. Examples of DNA polymerases that can be used in accordance with the methods described herein include *E. coli* DNA polymerase I, the large proteolytic fragment of *E. coli* DNA polymerase I, commonly known as "Klenow" polymerase, "Taq" polymerase, T7 polymerase, T4 polymerase, T5 polymerase, reverse transcriptase, etc.

Polymerases exhibiting processivity (the capacity to continue the extension of a particular primer to thereby produce an extension product of significant length) are preferred.

In several of the embodiments of the present invention, amplification is achieved by extending a hybridized primer on a single-stranded DNA template that is base paired to itself. Thus, polymerases capable of mediating such primer extension and strand displacement are particularly preferred. Examples of preferred polymerases include T5 DNA polymerase (Chatterjee, D. K. et al., *Gene* 97:13–19 (1991), T4 polymerase, and T7 polymerase. Where a DNA polymerase does not displace a base-paired stand of a DNA molecule and extend a primer into the previously base-paired region with sufficient efficiency, such capacity may be facilitated by the addition of an accessory protein. For example, the capacity of T7 polymerase to displace a strand of a base-paired molecule is enhanced by the presence of T7 gene 4 protein (Kolodner, R. et al., *J. Biol. Chem* 253:574–584 (1978)). Similarly, T4 DNA polymerase can catalyze extensive primer extension if the reaction additionally contains T4 gene 32 protein (Gillin, F. D. et al., *J. Biol. Chem* 251:5219–5224 (1976)). Use of the T7 promoter and gene 4 protein, however, has the advantage that the gene 4 protein is used catalytically rather than stoichiometrically during the primer extension reaction.

In some embodiments of the invention, amplification is achieved by extending a hybridized primer on a DNA template of a double-stranded DNA molecule composed of two separable strands. Thus, in such embodiments, polymerases capable of mediating such primer extension are preferred. Examples of preferred polymerases include those cited above. The capacity to extend primer molecules using such double-stranded DNA templates may be facilitated through the addition of topisomerases and/or gyrases (Eki, T. et al., *J. Biol. Chem* 266:3087–3100 (1991); Parada, C. A. et al., *J. Biol. Chem* 264:15120–15129 (1989)).

When an enzymatic reaction, such as a polymerization reaction, is being conducted, it is preferable to provide the components required for such reaction in "excess" in the reaction vessel. "Excess" in reference to components of the amplification reaction refers to an amount of each component such that the ability to achieve the desired amplification is not substantially limited by the concentration of that component.

A "ligase" is an enzyme that is capable of covalently linking the 3' hydroxyl group of a nucleotide to the 5' phosphate group of a second nucleotide. Ligases capable of joining "blunt ended" or "staggered ended" double-stranded nucleic acids, may be employed. Examples of suitable ligases include *E. coli* DNA ligase, T4 DNA ligase, etc.

The present invention employs a "recombinase," and most preferably, a "site-specific recombinase." As used herein, a recombinase is an enzyme whose action on two nucleic acid molecules results in recombination between the two molecules. Recombination is a well-studied natural process which results in the scission of two nucleic acid molecules having identical or substantially similar (i.e. "homologous") sequences, and the reformation of the two molecules such that one region of each initially present molecule becomes ligated to a region of the other initially present molecule (Sedivy, J. M., *Bio-Technol.* 6:1192–1196 (1988), which reference is incorporated herein by reference). Recombinases are naturally present in both prokaryotic and eucaryotic cells (Smith, G. R., In: *Lambda II*, (Hendrix, R. et al., Eds.), Cold Spring Harbor Press, Cold Spring Harbor, N.Y., pp. 175–209 (1983), herein incorporated by reference)).

Two types of recombinational reactions have been identified. In the first type of reaction, "general" or "homologous" recombination, any two homologous sequences can be recognized by the recombinase (i.e. a "general recombinase"), and can thus act as substrates for the reaction. In contrast, in the second type of recombination, termed "site-specific" recombination, the recombinase can catalyze recombination only between certain specialized "recombinational sites." Thus, in "site-specific recombination," only homologous molecules having a particular sequence may act as substrates for the reaction.

Site specific recombination is thus mediated by a site-specific recombinase acting on two "recombinational sites." Several such site-specific recombination systems have been described. The most preferred site-specific recombinational system is the site-specific recombination system of the *E. coli* bacteriophage P1. The P1 bacteriophage cycles between a quiescent, lysogenic state and an active, lytic state. The bacteriophage's site-specific recombination system catalyzes the circularization of P1 DNA upon its entry into a host cell. It is also involved in the breakdown of dimeric P1 DNA molecules which may form as a result of replication or homologous recombination.

The P1 site-specific recombination system catalyzes recombination between specialized "recombinational sites" known as "lox" sites (e.g., "loxP," "loxB" etc.). The loxP site is the preferred lox site of the present invention has been shown to consist of a double-stranded 34 bp sequence. This sequence contains two 13 bp inverted repeated sequences which are separated from one another by an 8 bp spacer region (Hoess, R. et al., *Proc. Natl. Acad. Sci.* (U.S.A.) 79:3398–3402 (1982); Sauer, B. L., U.S. Pat. No. 4,959,317, herein incorporated by reference).

The recombination of lox sites is mediated by a P1-encoded protein known as "Cre" (Hamilton, D. L. et al., *J. Molec. Biol.* 178:481–486 (1984), herein incorporated by reference). The Cre protein mediates recombination between two loxP sequences (Sternberg, N. et al., *Cold Spring Harbor Syrup. Quant. Biol.* 45:297–309 (1981)). These sequences may be present on the same DNA molecule, or they may be present on different molecules. Cre protein has a molecular weight of 35,000. The protein has been purified to homogeneity, and its reaction with the loxP site has been extensively characterized (Abremski, K. et al., *J. Molec. Biol.* 259:1509–1514 (1984), herein incorporated by reference). The cre gene (which encodes the Cre protein) has been cloned (Abremski, K. et al., *Cell* 32:1301–1311 (1983), herein incorporated by reference). Plasmids producing Cre may be obtained from Life Technologies, Inc. (Gaithersburg, Md.).

Any protein that is capable of mediating recombination between two lox sites is the functional equivalent of Cre protein. Any nucleotide sequence that can be recombined with a lox sequence by Cre is the functional equivalent of a lox site.

The site specific recombination catalyzed by the action of Cre protein on two lox sites is dependent only upon the presence of the above-described lox sites and Cre. No energy is needed for this reaction; thus, there is no requirement for ATP or other similar high energy molecules. Moreover, no factors or proteins other than the Cre protein is required in order to mediate site-specific recombination at lox sites (Abremski, K. et al., *J. Molec. Biol. Chem.* 259:1509–1514 (1984)). In vitro, the reaction is highly efficient; Cre is able to convert 70% of the DNA substrate into products and it appears to act in a stoichiometric manner (Abremski, K. et al., *J. Molec. Biol. Chem.* 259:1509–1514 (1984)).

Cre-mediated recombination can occur between lox sites which are present on two different molecules. Because the internal spacer sequence of the loxP site is asymmetrical, two loxP sites exhibit directionality relative to one another (Hoess, R. H. et al., *Proc. Natl. Acad. Sci.* (U.S.A.) 81:1026–1029 (1984)). If the loxP sites are in the same relative orientation, Cre acts to excise and circularize the DNA between them. If the sites are in an opposite relative orientation, Cre acts to flip the DNA between them. The recombinational event works efficiently on linear or circular molecules (Abremski, K. et al., *Cell* 32:1301–1311 (1983); Abremski, K. et al., *J. Molec. Biol. Chem.* 261:391–396 (1986)).

The nature of the interaction between Cre and lox sites has been extensively studied (Hoess, R. P. et al., *Cold Spring. Harb. Symp. Quant. Biol.* 49:761–768 (1984), herein incorporated by reference). In particular, mutations have been produced both in Cre, and in the lox site.

The Cre mutants thus far identified have been found to catalyze recombination at a much slower rate than that of the wild-type Cre protein. lox mutants have been identified which recombine at lower efficiency than the wild-type site (Abremski, K. et al., *J. Molec. Biol. Chem.* 261:391–396 (1986); Abremski, K. et al., *J. Molec. Biol.* 202:59–66 (1988), herein incorporated by reference).

Experiments with mutant lox sites in which either the left or right inverted repeat had been removed, has revealed that Cre is capable of binding to partial loxP sites, but is incapable of mediating efficient recombination between such sites. Insertions in the spacer region impair the ability of Cre to catalyze recombination. Of particular interest to the present invention is the use of a loxP511 mutant site.

The Cre protein is capable of mediating lox-specific recombination in eucaryotic hosts, such as *Saccharomyces cerevisiae* (Sauer, B., *Molec. Cell. Biol.* 7:2087–2096 (1987); Sauer. B. L., U.S. Pat. No. 4,959,317, herein incorporated by reference), or mammalian cells (Sauer, B. et al., *Proc. Natl. Acad. Sci.* (U.S.A.) 85:5166–5170 (1988), Sauer, B. et al., *Nucleic Acids Res.* 17:147–161 (1989), both references herein incorporated by reference).

Significantly, the lox-Cre system can mediate site-specific recombination between lox sites separated by extremely large numbers of nucleotides (Sauer, B. et al., *Gene* 70:331–341 (1988); Sternberg, N., *Proc. Natl. Acad. Sci.* (U.S.A.) 87:103–107 (1990); Sauer, B. et al., *Proc. Natl. Acad. Sci.* (U.S.A.) 84:9108–9112 (1987); Palazzolo, M. J. et al., *Gene* 88:25–36 (1990), all herein incorporated by reference).

It has been found that certain *E. coli* enzymes inhibit efficient circularization of linear molecules which contain two lox sites. Hence, enhanced in vivo circularization efficiency can be obtained through the use of *E. coli* mutants which lack exonuclease V activity (Sauer, B. et al., *Gene* 70:331–341 (1988)).

Although the Cre-lox site-specific recombination system is preferred, alternative site-specific recombination systems have been identified, and can be used in accordance with the methods of the present invention.

For example, the site-specific recombination system of the *E. coli* bacteriophage λ (Weisberg, R. et al., In: *Lambda II* (Hendrix, R. et al., Eds.), Cold Spring Harbor Press, Cold Spring Harbor, N.Y., pp. 211–250 (1983), herein incorporated by reference) can be employed. Bacteriophage λ uses its recombinational system in order to integrate its genome into its host, the bacterium *E. coli*. The system is also employed to excise the bacteriophage from the host genome in preparation for virus' lytic growth.

The λ recombination system is composed of four proteins- Int and Xis, which are encoded by the bacteriophage, and two host integrative factors encoded by the *E. coli*. These proteins catalyze site-specific recombination between "att" sites.

The λ Int protein (together with the *E. coli* host integration factors) will catalyze recombination between "attP" and "attB" sites. If the attP sequence is present on a circular molecule, and the attB site is present on a linear molecule, the result of the recombination is the disruption of both att sites, and the insertion of the entire attP-containing molecule into the attB site of the second molecule. The newly formed linear molecule will contain an attL and an attR site at the termini of the inserted molecule.

The λ Int enzyme is unable to catalyze the excision of the inserted molecule. Thus, the reaction is unidirectional. In the presence of the λ Xis protein, the reverse reaction can proceed, and a site-specific recombinational event will occur between the attR and attL sites to regenerate the initial molecules.

The nucleotide sequence of both the Int and Xis proteins are known, and both proteins (as well as the host integrative factors) have been purified to homogeneity. Both the integration and the excision reaction can be conducted in vitro (Better, M.; Wickner, S.; Auerbach, J. and Echols, H., *Cell* 32:161–168 (1983)). The nucleotide sequences of the four att sites has also been determined (Weisberg, R. et al., In: *Lambda II*, (Hendrix, R. et al., Eds.), Cold Spring Harbor Press, Cold Spring Harbor, N.Y., pp. 211–250 (1983), which reference has been herein incorporated by reference).

Additional site-specific recombination systems that may be employed include TpnI and the β-lactamase transposons (Levesque, R. C., *J. Bacteriol.* 172:3745–3757 (1990)); the Tn3 resolvase (Flanagan, P. M. et al., *J. Molec. Biol.* 206:295–304 (1989); Stark, W. M. et al., *Cell* 58:779–790 (1989)); the yeast recombinases (Matsuzaki, H. et al., *J. Bacteriol.* 172:610–618 (1990)); the *B. subtilis* SpoIVC recombinase (Sato, T. et al., *J. Bacteriol.* 172:1092–1098 (1990)); the Flp recombinase (Schwartz, C. J. et al., *J. Molec. Biol.* 205:647–658 (1989); Parsons, R. L. et al., *J. Biol. Chem.* 265:4527–4533 (1990); Golic, K. G. et al., *Cell* 59:499–509 (1989); Amin, A. A. et al., *J. Molec. Biol.* 214:55–72 (1990)); the Hin recombinase (Glasgow, A. C. et al., *J. Biol. Chem.* 264:10072–10082 (1989)); immunoglobulin recombinases (Malynn, B. A. et al., *Cell* 54:453–460 (1988)); and the Cin recombinase (Hafter, P. et al., *EMBO J.* 7:3991–3996 (1988); Hubner, P. et al., *J. Molec. Biol.* 205:493–500 (1989)), all herein incorporated by reference. Such alternate systems are discussed by Echols, H. (*J. Biol. Chem.* 265:14697–14700 (1990)), de Villartay, J. P. (*Nature* 335:170–174 (1988); Craig, N. L. (*Ann. Rev. Genet.* 22:77–105 (1988)), Poyart-Salmeron, C. et al. (*EMBO J.* 8:2425–2433 (1989)), Hunger-Bertling, K. et al. (*Molec. Cell. Blochem.* 92:107–116 (1990)), and Cregg, J. M. (*Molec. Gen. Genet.* 219:320–323 (1989)), all herein incorporated by reference.

Conditions or agents which increase the rate or the extent of priming, primer elongation, or strand displacement, may be used to increase the extent of the amplification obtained with the methods of the present invention. For instance, as indicated above, the addition of topoisomerases, helicases, gyrases or single-stranded nucleic acid binding proteins (such as the gene 32 protein of T4 or the gene 4 protein of T7) may be used to increase the strand displacement rate of a DNA polymerase, or may allow the use of a DNA polymerase that might not ordinarily give substantial amplification.

It is desirable to provide to the assay mixture an amount of required co-factors such as $Mg^{++}$, and dATP, dCTP, dGTP, TTP, ATP, CTP, GTP, UTP or other nucleotides in sufficient quantity to support the degree of amplification desired. Nucleotide analogues, etc. (Piccirilli, J. A. et al., *Nature* 343:33–37 (1990) can be substituted or added to those specified above, provided that the base pairing, polymerase and strand displacing functions are not adversely affected to the point that the amplification does not proceed to the desired extent.

II. THE MOLECULES EMPLOYED IN THE AMPLIFICATION METHOD

A. The Nature of the Target Molecule

The methods of the present invention may be used to amplify any desired target nucleic acid molecule. Such molecules may be either DNA or RNA. The molecule may be homologous to other nucleic acid molecules present in the sample (for example, it may be a fragment of a human chromosome isolated from a human cell biopsy, etc.). Alternatively, the molecule may be heterologous to other nucleic acid molecules present in the sample (for example, it may be a viral, bacterial, or fungal nucleic acid molecule isolated from a sample of human blood, stools, etc.). The methods of the invention are capable of simultaneously amplifying both heterologous and homologous molecules. For example, amplification of a human tissue sample infected with a virus may result in amplification of both viral and human sequences.

The present methods do not require that the desired target molecule have any particular sequence or length. In particular, the molecules which may be amplified include any naturally occurring procaryotic (for example, pathogenic or non-pathogenic bacteria, Escherichia, Salmonella, Clostridium, Agrobacter, Staphylococcus and Streptomyces, Streptococcus, Rickettsiae, Chlamydia, Mycoplasma, etc.), eucaryotic (for example, protozoans and parasites, fungi, yeast, higher plants, lower and higher animals, including mammals and humans) or viral (for example, Herpes viruses, HIV, influenza virus, Epstein-Barr virus, hepatitis virus, polio virus, etc.) or viroid nucleic acid. The nucleic acid molecule can also be any nucleic acid molecule which has been or can be chemically synthesized. Thus, the desired target nucleic acid sequence need not be found in Nature.

The target nucleic acid molecule which is to be amplified may be in either a double-stranded or single-stranded form. If the nucleic acid is double-stranded at the start of the amplification reaction it may be first treated to render the two strands into a single-stranded, or partially single-stranded, form. Methods are known to render double-stranded nucleic acids into single-stranded, or partially single-stranded, forms, such as heating, or by alkali treatment, or by enzymatic methods (such a by helicase action, etc.), or by binding proteins, etc. General methods for accomplishing this treatment are provided by Maniatis, T., et at. (In: *Molecular Cloning, A Laboratory Manual,* Cold Spring Harbor Laboratories, Cold Spring Harbor, N.Y. (1982)), and by Haymes, B. D., et al. (In: *Nucleic Acid Hybridization, A Practical Approach,* IRL Press, Washington, D.C. (1985)), which references are herein incorporated by reference. Such treatment permits the obtained single-stranded molecules to be amplified using the recombinational-site-containing primer molecules described below. Alternatively, double-stranded target molecules may be ligated into circular or linear double-stranded molecules that contain recombinational sites.

Single-stranded RNA, double-stranded RNA or mRNA are also capable of being amplified by the method of the invention. For example, the RNA genomes of certain viruses can be converted to DNA by reaction with enzymes such as reverse transcriptase (Maniatis, T. et al., *Molecular Cloning (A Laboratory Manual),* Cold Spring Harbor Laboratory, 1982; Noonan, K. F. et al., *Nucleic Acids Res.* 16:10366 (1988)). The product of the reverse transcriptase reaction may then be amplified according to the invention.

The complete nucleotide sequence of the desired molecule need not be known in order to employ the methods of the present invention. The present invention requires knowledge only of the sequences that flank the sequence that is to be amplified. The target polynucleotide that is to be amplified may thus be envisioned as consisting of three regions. The first region, corresponding to the 3' terminus of the desired molecule that is to be amplified is the region to which the single-primer of the present invention hybridizes, or to which double-stranded ligation adaptors are added. Thus, the sequence of this first region must be ascertained in order to construct a complementary primer that would be capable of hybridizing to the desired molecule.

As used herein, two sequences are said to be able to hybridize to one another if they are complementary and are thus capable of forming a stable anti-parallel double-stranded nucleic acid structure. Conditions of nucleic acid hybridization suitable for forming such double stranded structures are described by Maniatis, T., et al. (In: *Molecular Cloning, A Laboratory Manual,* Cold Spring Harbor Laboratories, Cold Spring Harbor, N.Y. (1982)), and by Haymes, B. D., et al. (In: *Nucleic Acid Hybridization, A Practical Approach,* IRL Press, Washington, D.C. (1985)). For the purpose of the present invention, the sequences need not exhibit precise complementarity, but need only be sufficiently complementary in sequence to be able to form a stable double-stranded structure. Thus, departures from complete complementarity are permissible, so long as such departures are not sufficient to completely preclude hybridization to form a double-stranded structure.

The size of the first region of the target molecule is such as to permit a primer molecule to stably hybridize to it. Preferably, therefore, the first region of the desired molecule will be greater than 10 nucleotides in length, and most preferably, 15 to 50 nucleotides in length. Longer or shorter primers may be used, however. The use of shorter primers may result in the amplification of nucleic acid sequences in addition to that of the desired sequence. The use of longer primers may slow the rate of hybridization. Extension of the primer may be done with reverse transcriptase where the desired molecule is present as RNA. Alternatively, such extension can be accomplished with other DNA polymerases where the desired molecule is DNA. If the first region is not used as a template for a primer, it need not be of a length sufficient to permit stable priming.

The second region of the desired molecule is located 5' to the first region, and consists of the central portion of the desired molecule. The second region of the desired molecule may have any sequence, and be of any length. As stated above, the sequence of this region need not be known in order to follow the methods of the present invention. Typically, the second region may extend from a few nucleotides to several kilobases.

The third region of the desired molecule is located at the 5' terminus of the desired molecule. The sequence of this region must be known in order to follow the methods of the present invention. Typically, the third region may extend from as few as 3 nucleotides to 10–20. If the third region is not used as a template for a primer, it need not be of a length sufficient to permit stable priming. In a preferred embodiment, however, the third region must be of sufficient length to permit stable hybridization to occur. In this embodiment, the third region is preferably of a length of 15 to 50 nucleotides in length. Longer or shorter primers may be used, however.

Thus, the extent of sequence information of the desired molecule that is needed to practice the present invention is typically less than that needed to practice PCR methods.

B. The Nature of the Single Primer

In its most preferred embodiments, the present invention employs a single primer to achieve the amplification of the desired molecule. This single primer is also referred to herein as a "first primer," in order to distinguish it from other primers that optionally may be employed. The single primer molecule is of suitable length to stably hybridize to the first region of the desired molecule. Primer molecules of 10–50 nucleotides are thus suitable. In a most preferred embodiment, the primer molecule will comprise from 3' terminus to 5' terminus:

(1) a first polynucleotide region complementary to the 3' terminus of the target polynucleotide region;

(2) a second polynucleotide region containing modified nucleotides (especially methylated nucleotides or (α-thio)phosphorothioate nucleotides, wherein, if the second polynucleotide region were hybridized to a complementary polynucleotide, a double-stranded polynucleotide would thereby be formed that would contain one or more restriction endonuclease cleavage sites that would be recognized by a restriction endonuclease that is substantially incapable of cleaving a strand of a nucleic acid molecule that contains the modified nucleotides; and (3) a third polynucleotide region, wherein, if the third polynucleotide region were hybridized to a complementary polynucleotide, a double-stranded polynucleotide would thereby be formed that would contain a recombinational site (especially a lox site);

In a highly preferred sub-embodiment, the single primer will additionally contain a fourth polynucleotide region, the fourth polynucleotide region of the first primer molecules being located 5' to the third polynucleotide region of the first primer molecules, and having a nucleotide sequence complementary thereto, such that the third and fourth polynucleotide regions of the first primer molecules are hybridized to one another forming a complete or (more preferably) a partial recombinational site.

Any of a variety of methods can be used to produce the primer molecule. For example, the molecule can be excised from a vector that contains it using suitable enzymes, such as restriction enzymes. Most preferably, however, the primer will be made synthetically, using well-known chemical methods.

Since the lox site is the most preferred recombinational site of the present invention, the following description illustrates the invention by reference to the lox recombinational site. It will, however, be recognized that any of the above-described recombinational sites may be alternatively employed.

C. The Adaptor Molecules of the Invention

The above-described single primer is preferably employed in concert with a target polynucleotide that has been adapted to be a part of a circular double-stranded DNA molecule that comprises: (a) a lox site; (b) the target polynucleotide region; and (c) a hemi-modified restriction site located between the target polynucleotide region and the lox site, wherein one strand of the hemi-modified restriction contains modified nucleotides (especially methylated nucleotides and (α-thio)phosphorothioate nucleotides), such that a restriction endonuclease that recognizes such restriction site will be incapable of cleaving that strand containing the modified nucleotides, but will cleave that stand lacking modified bases (or vice versa).

Figure 11:
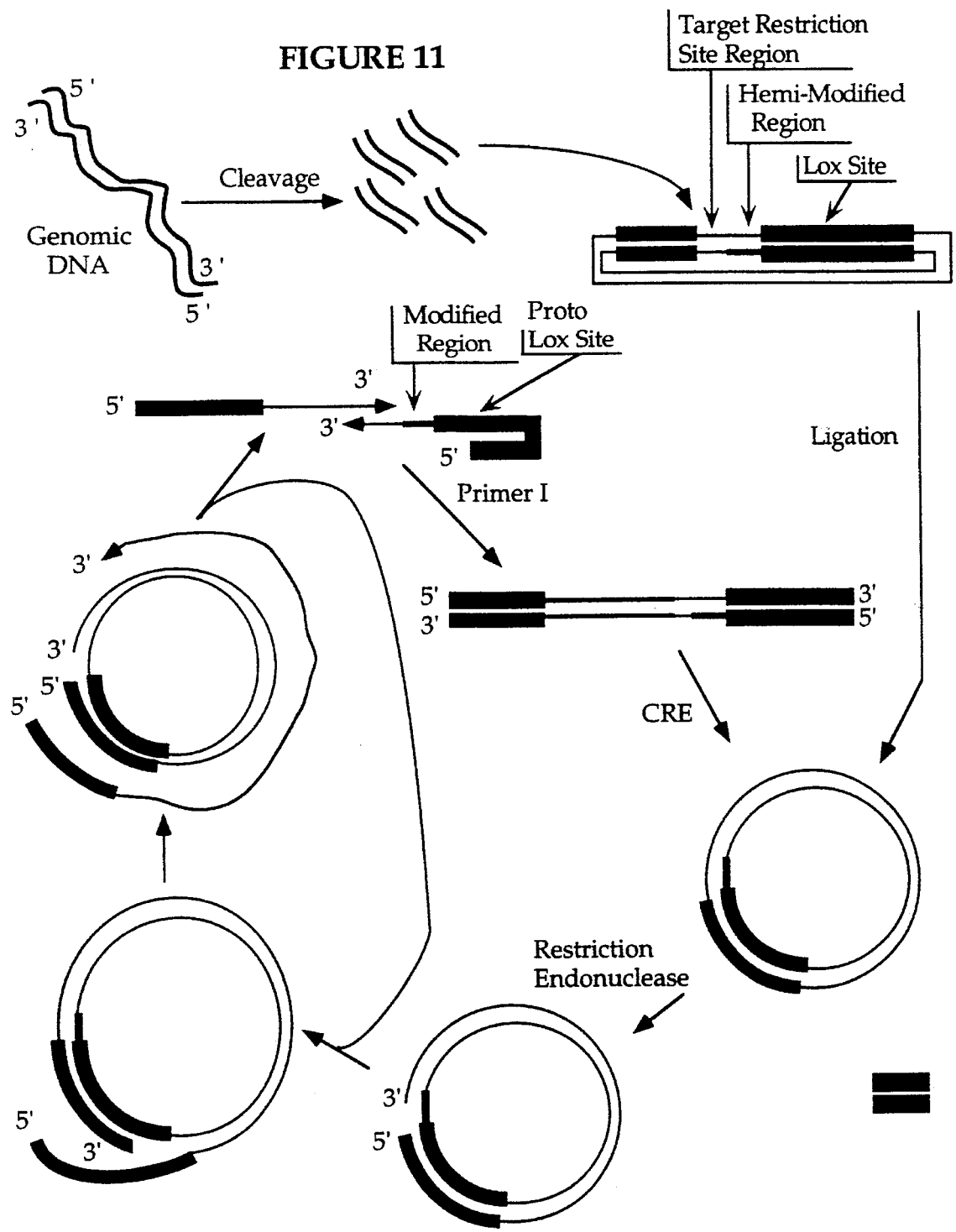
FIG. 11 provides a diagramatic representation of the use of ligation to form double-stranded circular molecules.
Figure 12:
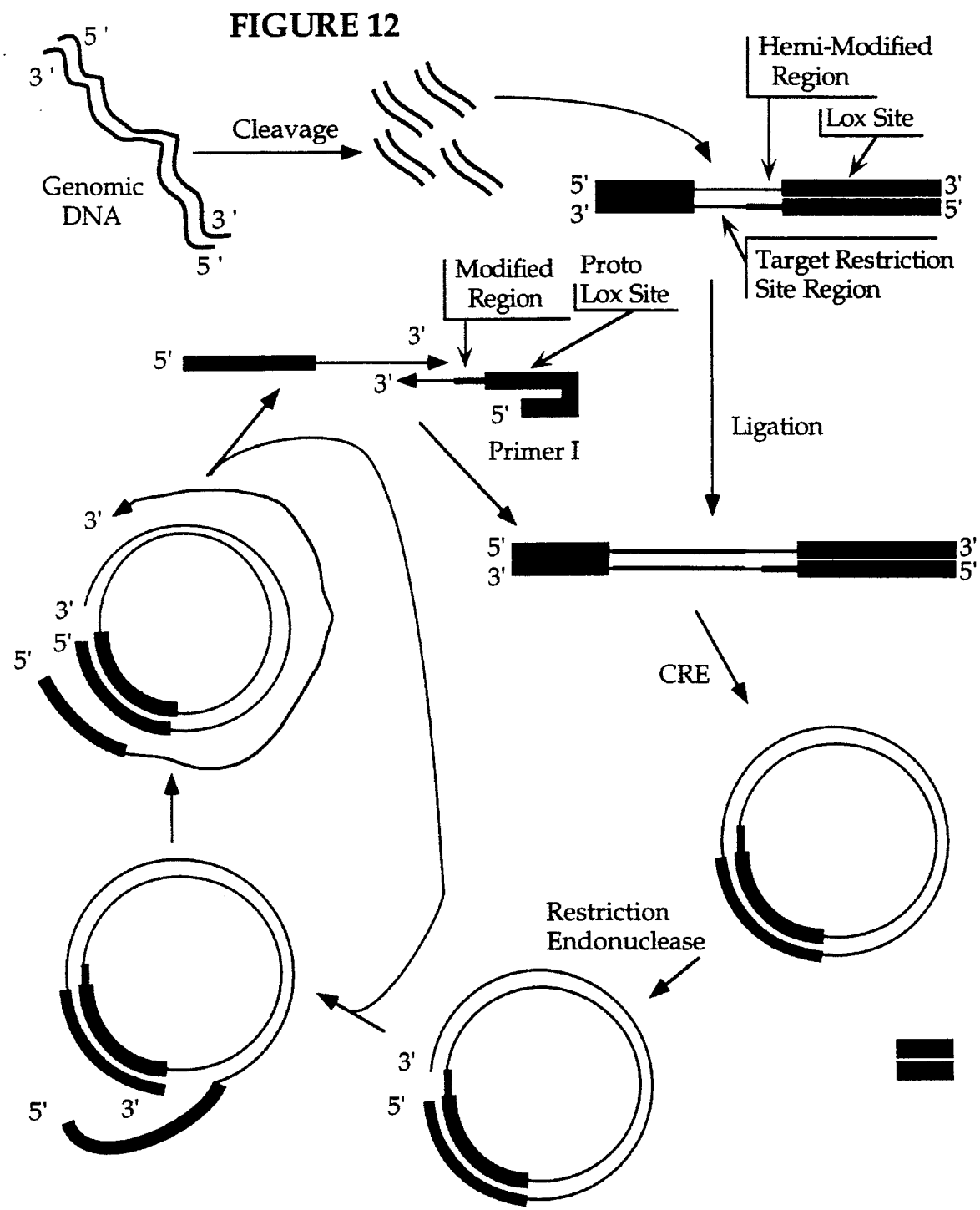
FIG. 12 provides a diagramatic representation of an alternative use of ligation to form double-stranded circular molecules.

Such a double-stranded circular molecule can be obtained in any of a variety of ways (see FIGS. 11 and 12). In one embodiment, a circular double-stranded DNA precursor molecule comprising: (a) a lox site; (b) a target restriction endonuclease cleavage site; and (c) a hemi-modified restriction site located between the target restriction endonuclease cleavage site and the lox site will be employed. The target polynucleotide is introduced (e.g., via target restriction site cleavage and ligation) into such a circular precursor molecule in order to form the desired double-stranded circular molecule. In employing such a circular precursor molecule, the molecule's lox site must be oriented (3'→5') opposite to the orientation of the single primer (such that if that strand of the desired circular molecule that lacks modified nucleotides were linearized by cleavage at the hemi-modified restriction site, and were hybridized to the single primer, primer extension of the linearized molecule would yield a linear double-stranded molecule having a lox site at each end that would be in direct orientation with respect to one another (see, FIG. 11).

In an alternative embodiment, such a double-stranded circular molecule is obtained via Cre-mediated recombination of a linear double-stranded DNA molecule that comprises: (a) a first lox site located at a first end of the linear molecule, (b) a second lox site located at a second end of the linear molecule, wherein the first and the second lox sites are directly oriented with respect to one another so as to permit the Cre to mediate the circularization of the linear double-stranded molecules, and to thereby form the double-stranded circular molecule; (c) the target polynucleotide region located internal to the first and second lox sites; and (d) a hemi-modified restriction site located between the target polynucleotide region and one of the tox sites, wherein one strand of the hemi-modified restriction site of each of the linear molecules contains modified nucleotides (especially methylated nucleotides and (α-thio)phosphorothioate nucleotides), such that a restriction endonuclease that recognizes such restriction site will be incapable of cleaving that strand containing the modified nucleotides (see, FIG. 12).

In a sub-embodiment, such a linear molecule may be obtained by inserting the target polynucleotide into a target restriction endonuclease site of a precursor double-stranded linear nucleic acid molecule that comprises: (a) a first lox site located at a first end of the linear molecule, (b) a second lox site located at a second end of the linear molecule, wherein the first and the second lox sites are directly oriented with respect to one another so as to permit the Cre to mediate the circularization of the linear double-stranded molecules, and to thereby form the double-stranded circular molecule; (c) a target restriction endonuclease cleavage site; and (d) a hemi-modified restriction site located between the target restriction site and one of the lox sites.

In alternative embodiments, such linear molecules may be obtained using one or more specialized "adaptor molecules." Such adaptor molecules alter the 3' and 5' termini of the target molecule in order to install the lox sites and hemi-modified restriction site onto the target molecule.

Such adaptor molecules may be either partially single-stranded, partially double-stranded nucleic acid molecules, completely single-stranded or completely double-stranded molecule. Thus, in one embodiment, the adaptation of the 5' terminus is accomplished by employing a primer molecule whose 5' terminus is designed such that it contains the desired adaptation. In a second embodiment, the 5' terminus of the primer extension product is altered (e.g., via lifation) using a 5' adaptor molecule. With respect to the alteration of the 3' terminus of the primer extension product, such alteration can be accomplished using either a single adaptor molecule, or, in an alternate embodiment with a pair of adaptor molecules having similar structure (and resulting in a mixture of primer extension products, some of which have been modified by one of the 3' adaptor molecules, and some of which have been modified by the other 3' adaptor molecule). Thus, for example, a linear double-stranded nucleic acid molecule containing the desired sequence may be incubated in the presence of ligase and double-stranded nucleic acid adaptor molecules so as to cause the adaptation of both ends of the linear molecule. Alternatively, such adaptation may be accomplished using primers and a polymerase-mediated primer extension reaction. In a third alternative, a combination of ligation (to adapt one end of the linear nucleic acid molecule containing the desired sequence) and primer extension (to adapt the linear molecule's other end) may be employed.

The adaptor molecules permit the linear molecule to form either single-stranded or double-stranded circular nucleic acid molecules which may be readily amplified under isothermal conditions.

1) Illustrative Adaptor Molecules of the 5' Terminus

Any of a variety of adaptor molecules may be used to modify the 5' terminus of the primer molecule or the primer extension product such that it contains a recombinational site, most preferably a lox site.

The adaptor molecule of the 5' terminus can be added to the primer molecule either before or after its template dependent extension. In the most preferred embodiment, a primer molecule is employed that has been modified to contain the 5' adaptor molecule. Thus, in this embodiment, the primer may be synthesized such that it contains an additional region (including the recombinational site) at its 5' terminus. If desired, when employing a recombinational site that, like lox exhibits directionality, some of the primer may be synthesized with the lox site in one orientation, and some of the primer synthesized with the lox site in the opposite orientation. Alternatively, 5' adaptor primer molecules that all have their recombinational site in a single orientation can be used in conjunction with 3' adaptor molecules that contain their recombinational site in an appropriate orientation.

Alternatively, however, the 5' terminus can be modified through the action of a ligase using either single-stranded or, more preferably, double-stranded DNA containing the recombinational site. In one embodiment, such ligation substrates will possess a 5' terminus (such as a 5' hydroxyl group)that prevents the ligation of more than one such ligation substrate molecule to the primer extension molecule. Alternatively, the adaptor molecule may be a single-stranded molecule, that exhibits intra-strand hybridization (i.e. a "hairpin" loop). As in the case of the adapted primer molecule discussed above, the use of a recombinational site having directionality will generally require the use of two hairpin loop species having opposite orientations for their recombinational sites. Alternatively, one may ligate a double-stranded molecule having the above-described attributes of the single-stranded 5' adaptor to one end of the linear double-stranded molecules of the sample. Additional sequences may, if desired, be added 3' or 5' of the recombinational site. Examples of suitable 5' adaptor molecules are shown in FIG. 1.

2) Illustrative Adaptor Molecules of the 3' Terminus

Figure 2A:
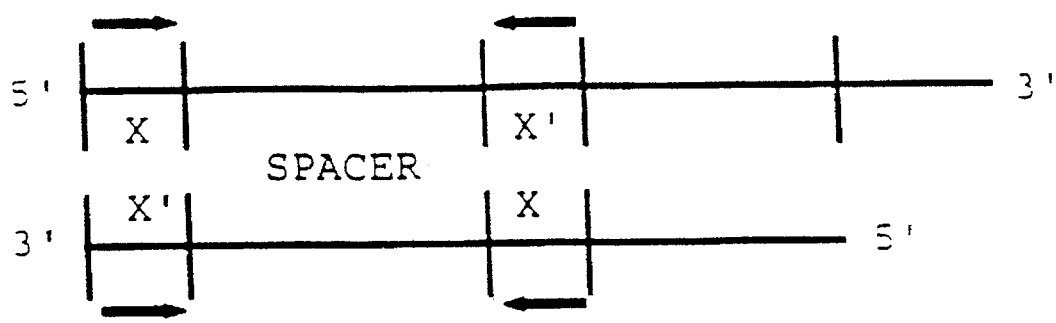
FIGS. 2A and 2B (comprising Drawings A,B,C and D) show examples of suitable 3' adaptor molecules.
Figure 2A:
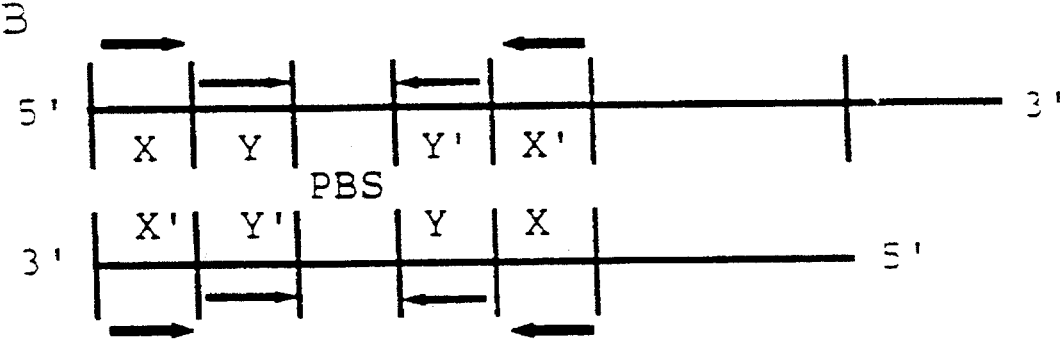
Figure 2A:
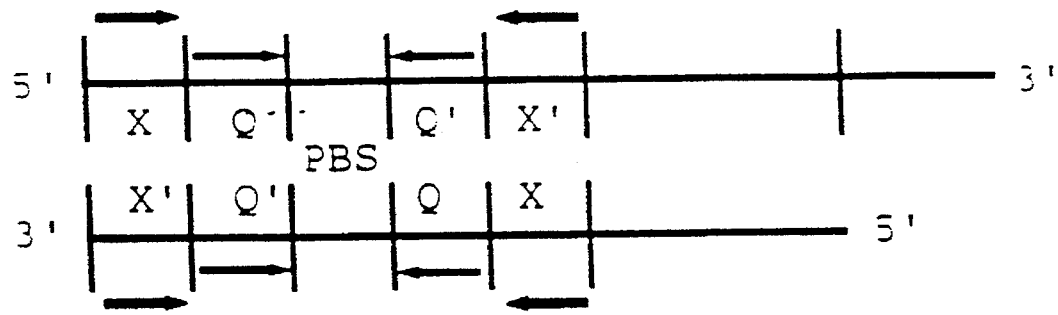
Figure 2B:
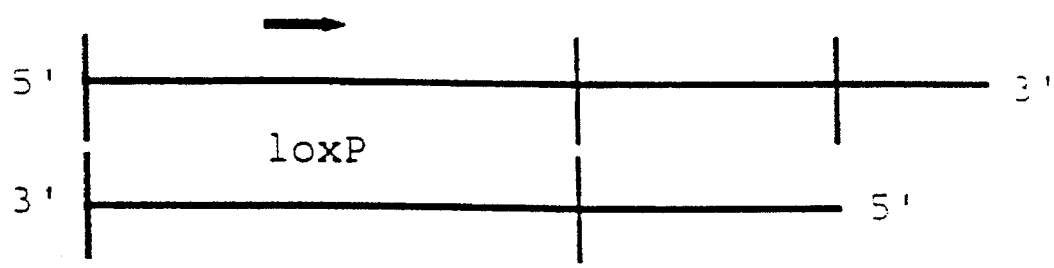
Figure 2B:
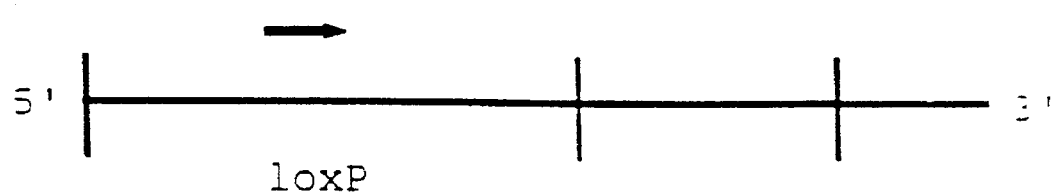
Figure 2B:
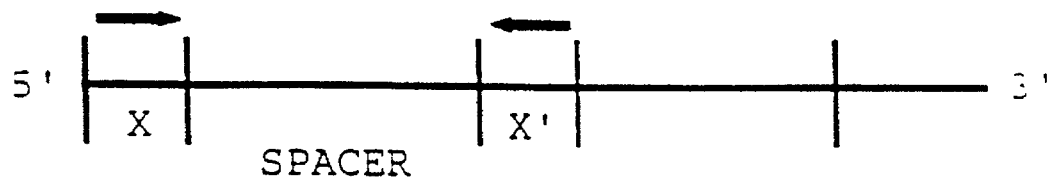
Figure 2B:
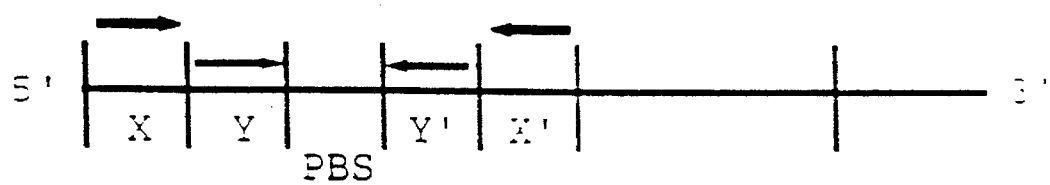
Figure 2B:
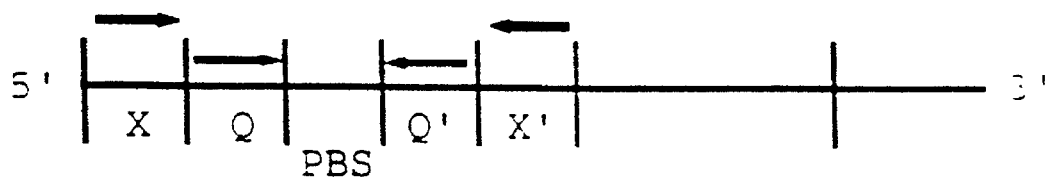

Any of a variety of different adaptor molecules can be used to alter the 3' terminus of the primer extension molecule. The choice of which type of adaptor molecule to use will depend upon whether the formation of single-stranded or double-stranded molecules is preferred. Examples of suitable 3' adaptor molecules are shown in FIGS. 2A and 2B.

a) Adaptor Molecules for the Formation of Single-Stranded Circular Molecules: Use of Partially Single-Stranded and Partially Double-Stranded 3' Adaptor Molecules In one embodiment, a partially single-stranded and partially double-stranded nucleic acid adaptor molecule is employed to alter the 3' terminus of the primer extension product as a prelude to the formation of single-stranded circular molecules. A feature of such molecules is that they possess a 3' protruding region having a predefined sequence. The sequence of this protruding sequence is selected such that 3'-most portion of the region has the same sequence as that of the third region of the desired molecule. In a first preferred sub-embodiment, this protruding terminus is blocked, as by the use or presence of a dideoxynucleotide, etc., such that it is incapable of being extended by a polymerase in a template-directed process.

The strand of the adaptor molecule that contains the 3' protruding sequence may be composed of RNA, such that it can be readily degraded by the inclusion of RNAse to the reaction, or by alkali treatment. Methods of forming RNA oligonucleotides are disclosed by Sharmeen, L. et al. (*Nucleic Acids Res.* 15:6705–6711 (1987)) and by Milligan, J. F., et al., *Nucleic Acids Res.* 15:8783–8798 (1987)). In another embodiment, the strand of the adaptor molecule that contains this protruding sequence is composed of a nucleic acid that has been biotinylated, such that the strand can be selectively removed from the reaction by addition of agents such as anti-biotin antibodies, avidin, streptavidin, etc.

A second feature of the adaptor molecules is the presence of a double-stranded region located 5' to the above-described protruding 3' terminus.

In one embodiment, the invention employs a single such 3' terminus adaptor molecule whose double-stranded region comprises a pair of inverted repeated sequences, preferably separated by a spacer sequence. This aspect of the invention is shown in FIG. 2A (Drawing A), wherein the terms X and X' are used to designate complementary sequences that comprise the inverted repeated sequence. The spacer sequence is preferably 3–100 nucleotides in length. The length of the spacer is selected such that the inverted repeated sequences are sterically capable of hybridizing to one another. Thus, if the inverted repeated sequences are of sufficient length, the sequences will be capable of hybridizing to one another in the absence of a spacer sequence. In a preferred embodiment, however, the spacer sequence is 10–50 nucleotide long, and preferably not an inverted repeated sequence. In this embodiment, the spacer sequence is adapted to function as a primer binding site (designated "PBS" in the Figures) for the amplification of the desired sequence.

In an alternate preferred embodiment, the invention employs two different 3' terminus adaptor molecules. In each of these adaptor molecules, the spacer sequence is composed of a second pair of inverted repeated sequences, such that the structure of the adaptor molecule provides a pair of external inverted repeated sequences that flank a pair of internal inverted repeated sequences. In a preferred embodiment, the sequences of the pair of internal inverted repeated sequences are interrupted by a primer binding site that is preferably 10–50 bases long, and preferably not an inverted repeated sequence. This aspect of the invention is shown in FIG. 2A (Drawing B) and FIG. 2B (Drawing D), where the term "PBS" is used to designate the relative position of the optional primer binding site, the terms Y and Y' or Q and Q' are used to designate complementary sequences that comprise the optional internal inverted repeated sequences, and the terms X and X' are used to designate complementary sequences that comprise the external inverted repeated sequences. In the most preferred sub-embodiment of this embodiment, the sequences of the external and internal repeated sequences are different. The sequences of the two adaptor molecules are selected such that the nucleotide sequence of the external inverted repeat sequence of the first of the two adaptor molecules is different from the external inverted repeated sequence of the second of the two adaptor molecules. The sequences of the external inverted repeats of the first and second adaptor molecules are thus selected such that they are substantially incapable of hybridizing to one another (i.e. the external repeat sequence of the first adaptor molecule is substantially incapable of hybridizing to the external inverted repeat of the second adaptor molecule). The nucleotide sequence of the internal inverted repeated sequences of the two adaptor molecules is preferably the same, or at least sufficiently similar to allow the respective internal repeated sequences of the adaptor molecules to hybridize to one another. If the internal repeated sequences are interrupted by a primer binding site, such sequences may be different, but will preferably be the same.

As used herein, two sequences are said to be "inverted repeats" of one another if they are complementary to one another. Similarly, an "inverted repeat sequence" is composed of two oligonucleofide or polynucleotide sequences ("arms") which are complimentary to one another. Thus, a feature of the adaptor molecules is that, although the inverted repeat sequences of the two strands of the double-stranded region of the adaptor molecules are hybridized to one another in the adaptor molecule, they would be capable of intra-strand hybridization (i.e. "snapping-back" and forming a hairpin loop structure) if the adaptor molecule were denatured or converted to a single-stranded form. The length of the inverted repeated sequences is selected such that intra-strand hybridization would be possible if the adaptor molecule were denatured or converted to a single-stranded form. Thus, the inverted repeated sequences are preferably greater than 10 nucleotides in length, and most preferably, 15 to 50 or more nucleotides in length. Longer or shorter inverted repeated sequences may however be used. The use of shorter inverted repeated sequences may result in a decreased rate of hairpin formation. The use of longer sequences may lead to a destablization of inter-strand hybridization, and thus may be undesirable where such hybridization is desired.

When defining conditions to be used in any specific embodiment of the present invention, it is desirable to select a primer that cannot prime on itself. To minimize the likelihood of potential interfering reactions, candidate primers should be tested in reactions which address this issue prior to use in the amplification process. One such example is to measure the addition of nucleotides by a polymerase to the 3' end of the candidate primer in the absence of any target molecule.

The above-described adaptor molecules can be synthesized using any of a variety of methods. For example, the "inverted repeated sequence-inverted repeated sequence," "inverted repeated sequence-spacer sequence-inverted repeated sequence" or the "external inverted repeated sequence-internal inverted repeated sequence-internal inverted repeated sequence-external inverted repeated sequence" segment of the adaptor molecules can be obtained by cloning such a sequence, propagating the vector, and then excising the sequence using a restriction endonuclease. The protruding 3' terminus can be formed using deoxynucleotide terminal transferase and the appropriate nucleotide triphosphates. In following such a method, it would be desirable to block the 3' terminus of the second strand of the adaptor molecule. Alternatively, the protruding 3' terminus can be added by ligating a single- or double-stranded molecule to the "inverted repeat-inverted repeat" segment of the adaptor molecule (or any of the above-described variants thereof), and then removing the sequence complementary to the "protruding 3' sequence" to thereby render that sequence actually protruding.

In a preferred embodiment, the strands of the adaptor molecule(s) are prepared separately (preferably by primer extension using suitable primers and templates, or by clonal propagation, by transcription, by synthetic means, or by any combination of these methods), and then mixed together under conditions sufficient to permit the molecules to hybridize to one another. This method is particularly suited to the embodiments wherein the strand that contains the protruding 3' end is RNA or is biotinylated. Those of ordinary skill will readily comprehend alternative methods for forming the adaptor molecules.

b) Adaptor Molecules for the Formation of Single-Stranded Circular Molecules: Use of Single-Stranded 3' Adaptor Molecules In a second, and preferred, sub-embodiment, the adaptor molecule(s) in the formation of single-stranded circular molecules will be single-stranded DNA (preferably biotinylated) or RNA molecules. Such molecules will have a sequence and structure that are identical to the structure of the that strand of the above-described partially single-stranded and partially double-stranded adaptor molecules which contain the discussed protruding 3' terminus. In the most preferred embodiment, the 3' terminus of the molecule is blocked, such that it cannot be extended by a polymerase.

3) Adaptor Molecules for the Formation of Double-Stranded Circular Molecules

The above-described 3' adaptor molecules are designed to permit the formation of single-stranded circular molecules. In order to form double-stranded circular molecules, a different type of 3' adaptor molecule is preferably employed.

In this embodiment of the invention, the 3' terminus of the primer extension product is modified such that it contains a recombinational site. If a site such as lox is employed, the orientation of the site must be such that upon adaptation, the two lox sites are present in a direct repeat orientation. For such purpose, a partially single-stranded and partially double-stranded adaptor molecule or a single-stranded molecule is employed. The partially single-stranded and partially double-stranded adaptor molecule will have a protruding 3' terminus that is capable of hybridizing to the primer extension product in the manner described above, and of being extended in a template-dependent manner. The double-stranded region of the molecule, located 5' to the protruding 3' terminus, will comprise a recombinational site. Most preferably, the double-stranded region will also contain a region that is substantially incapable of participating in inter-strand hybridization flanked by sequences that are capable of participating in such hybridization. Most preferably, such incapacity is obtained through the use of sequences that are identical, and have the attributes of the primer binding sequence discussed above. Such a molecule is illustrated in FIG. 2B (Drawing C). If a single-stranded 3' terminus adaptor molecule is employed, the molecule will preferably contain the same structure and sequence as that strand of the above-described partially single-stranded and partially double-stranded adaptor molecule that possess the protruding 3' terminus. Alternatively, one may ligate a double-stranded molecule having the above-described attributes of the single-stranded 3' adaptor to one end of the linear double-stranded molecules of the sample.

D. The Amplification Substrates

The present invention employs amplification substrate molecules in order to achieve the amplification of the desired molecule.

Any of a variety of amplification substrates may be employed. In one embodiment, such substrates are either the primer molecule used to form the primer extension product (i.e., a 5' adaptor primer (either containing or lacking the 5' recombinational site) or a sequence complementary to that of the optional primer binding site of the 3' terminus adaptor molecule. Most preferably, the substrate is a primer that contains the 5' adaptor molecule (including a recombinational site). The above-described single primer is the most preferred amplification substrate.

III. ILLUSTRATIVE AMPLIFICATION METHODS OF THE PRESENT INVENTION

A. Primer Extension Method

1. The First Step of the Method

In the first step of one embodiment of the amplification methods of the present invention, the nucleic acid molecules of the sample are incubated with the above-described single primer molecule in the presence of DNA polymerase, and requisite nucleotide triphosphates and co-factors. The molecules are incubated under conditions sufficient to permit the primer to hybridize to its target sequence, and to be extended to form a primer extension product. Thus, if the desired sequence is a double-stranded DNA or RNA molecule, the strands are separated as by heat denaturation, or other means. If the desired sequence is a single-stranded DNA or RNA molecule, the denaturation step may be omitted.

In one sub-embodiment of the invention, as for example when the concentration of the desired molecule is anticipated to be low, the molecules can be denatured and renatured in a cyclical manner so as to permit repeated rounds of primer extension. In this embodiment, the use of thermostable polymerases, such as Taq polymerase is preferred, so that the expense of adding new polymerase can be avoided.

Most preferably, the conditions of the primer extension will be controlled such that the average length of the extended single primers will be the length separating the beginning of the first region from the end of the third region of the desired molecule. Such controlling of conditions can be accomplished by altering the concentration of DNA polymerase, the duration of the polymerization reaction, or by limiting the concentration of a nucleotide triphosphate such that "stuttering" of the primer extension product occurs when it reaches the desired average length.

After single primer extension has been completed, the reaction is treated, preferably with heat or RNAse H (if the target molecule was RNA) so as to denature double-stranded nucleic acid molecules and render such molecules single-stranded. If desired, excess primer can be removed from the sample (as by filtration, adsorption, etc.), however, such action is not necessary to the invention.

2. The Second Step of the Methods: Adaptation of the 3' Terminus of the Primer Extension Product The second step of this embodiment of the method entails the adaptation of the primer extension product such that it is capable of conversion into a circular molecule. The adaptation of the 3' terminus may precede or follow the adaptation of the 5' terminus, depending upon the adaptor molecules selected. Adaptation of the termini may also be accomplished simultaneously. As indicated, the adaptation of the 5' terminus may be accomplished through the use of modified primers, and may thus be accomplished prior to the primer extension step.

a) Further Primer Extension

Figure 3A:
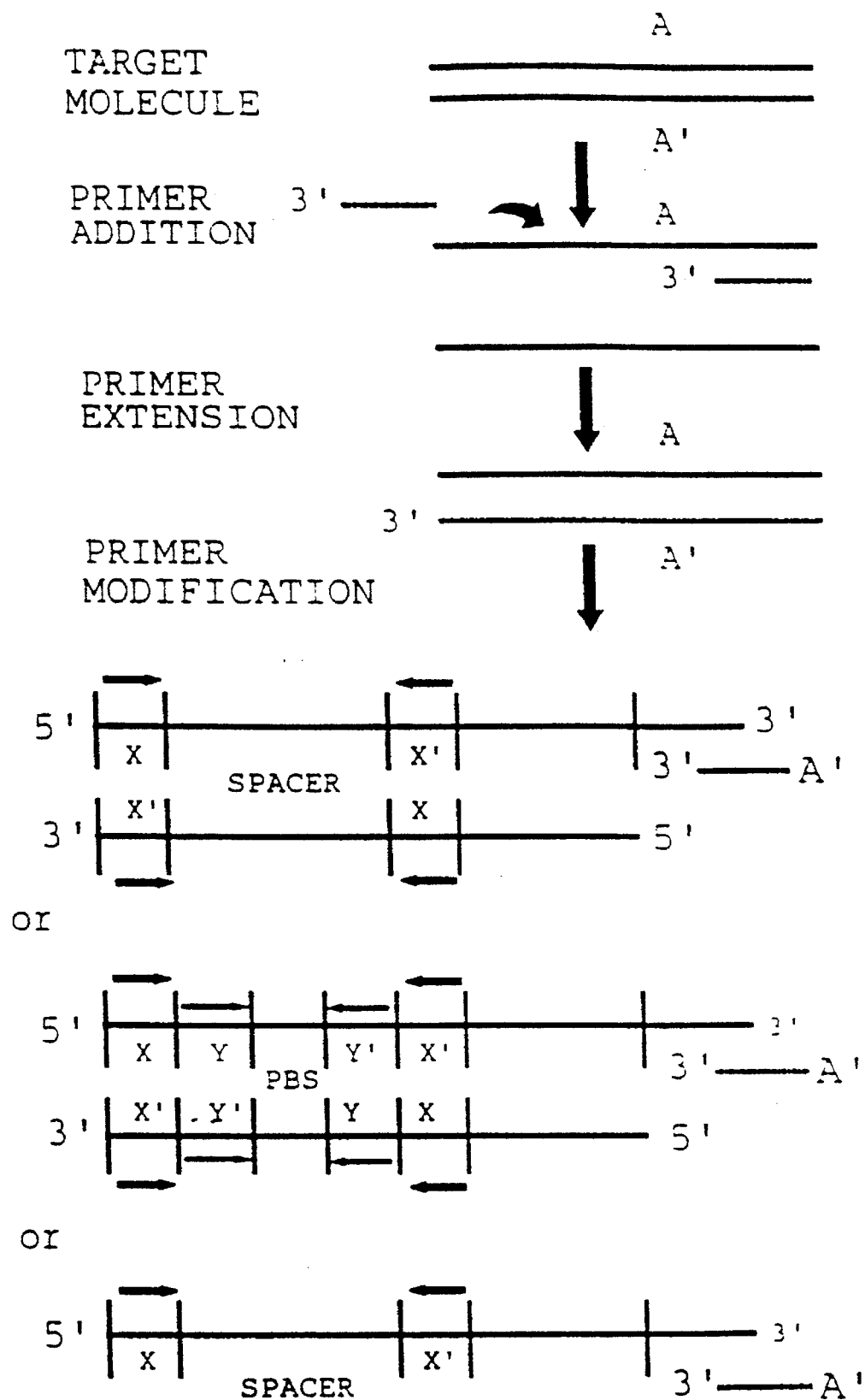
FIGS. 3A and 3B show the adaptation of the 3' terminus of the primer extension product. Lines A, B and C of FIG. 3A illustrate the use of different adaptor molecules to modify the 3' terminus of the primer extension product through further primer extension. Line D of FIG. 3B shows the use of ligation to modify the 3' terminus.

In a first and preferred sub-embodiment employing either the partially single-stranded/partially double-stranded 3' adaptor molecule(s) or the single-stranded 3' adaptor molecule(s), the adaptation of the 3' terminus of the primer extension product is accomplished through the further template-mediated extension of the primer extension products (FIG. 3A, lines A, B, C). Most preferably, the adaptor molecules used in this embodiment will contain blocked 3' termini.

In this embodiment, the primer extension products, which have been rendered single-stranded, are permitted to hybridize to the adaptor molecules. As indicated above, the molecules have regions of homology sufficient to permit the primer extension products to hybridize to the adaptor molecule.

Regardless of which type of adaptor molecule(s) is employed, the further extension of the primer extension products results in the formation of a partially-double-stranded and partially single stranded molecule. The molecule is characterized in possessing a protruding 5' terminus whose sequence comprises that of the primer extension product. If the adaptor molecule was partially double-stranded, the further extension of the primer extension product causes the displacement or destruction of the strand that was initially complementary to the template.

b) Ligation

Figure 3B:
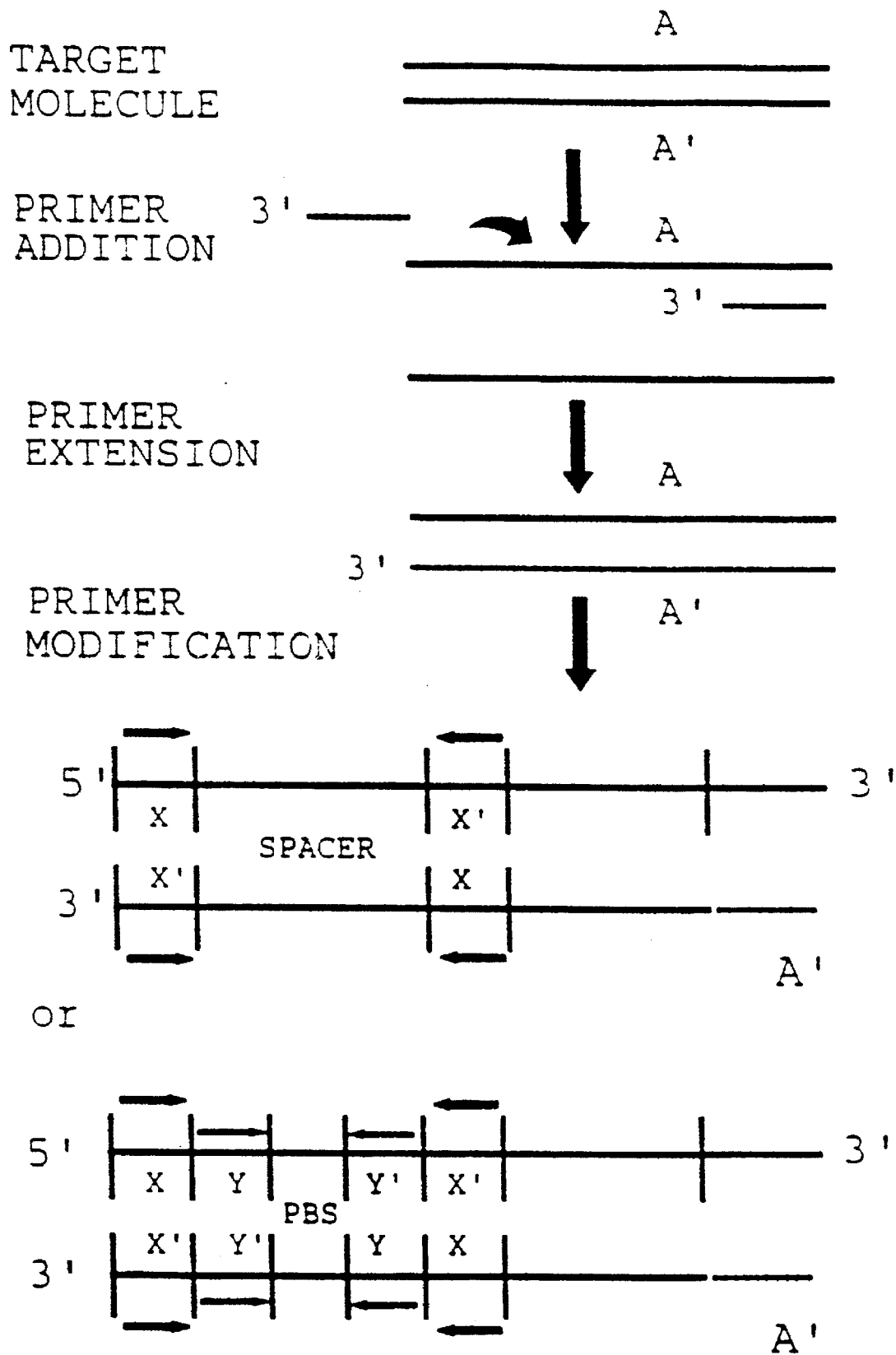
Figure 4A:
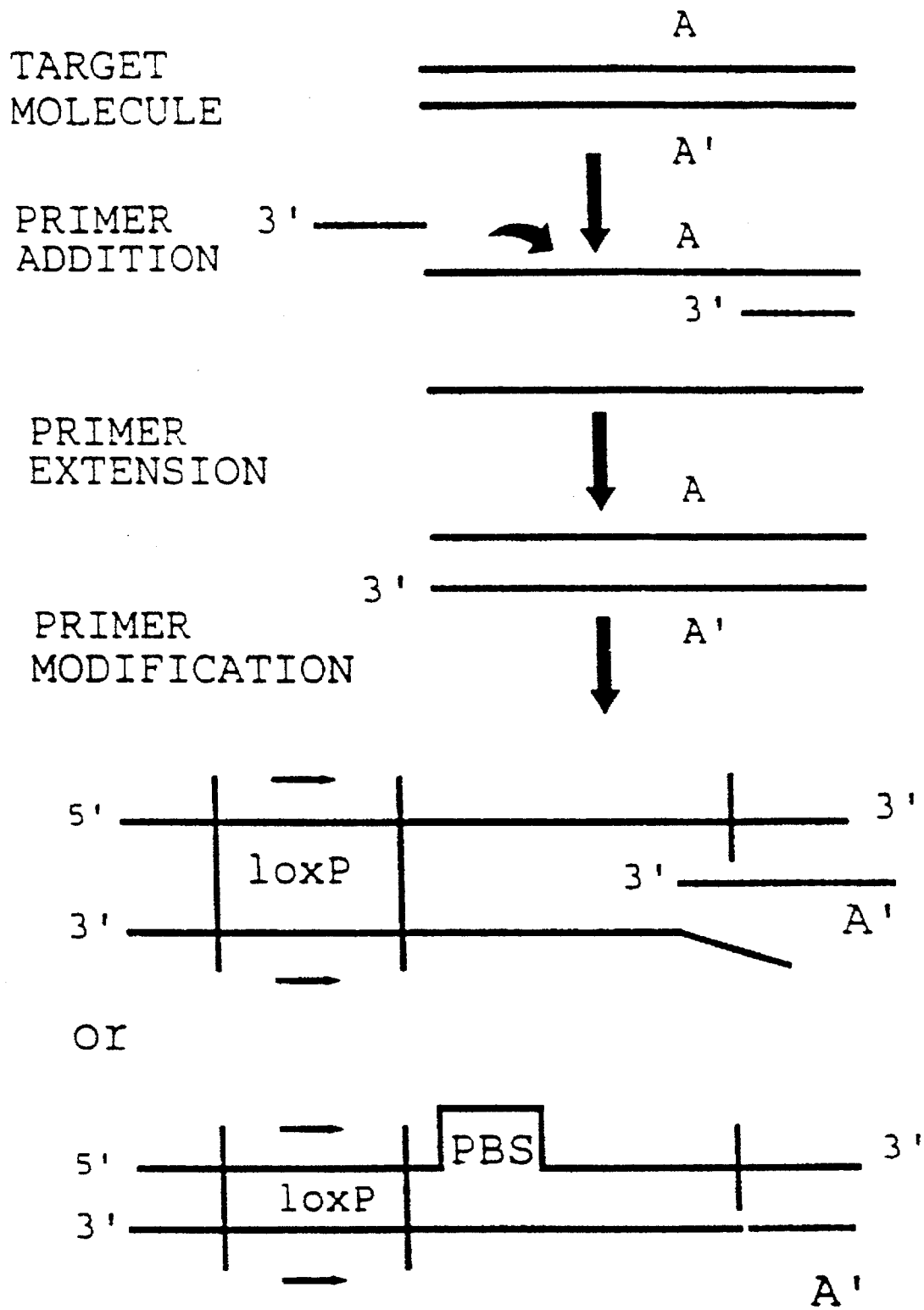
FIGS. 4A, 4B, 4C, and 4D show the formation of double-stranded circular molecules from linear molecules adapted using adaptor molecules that contain a recombinational site.
Figure 4B:
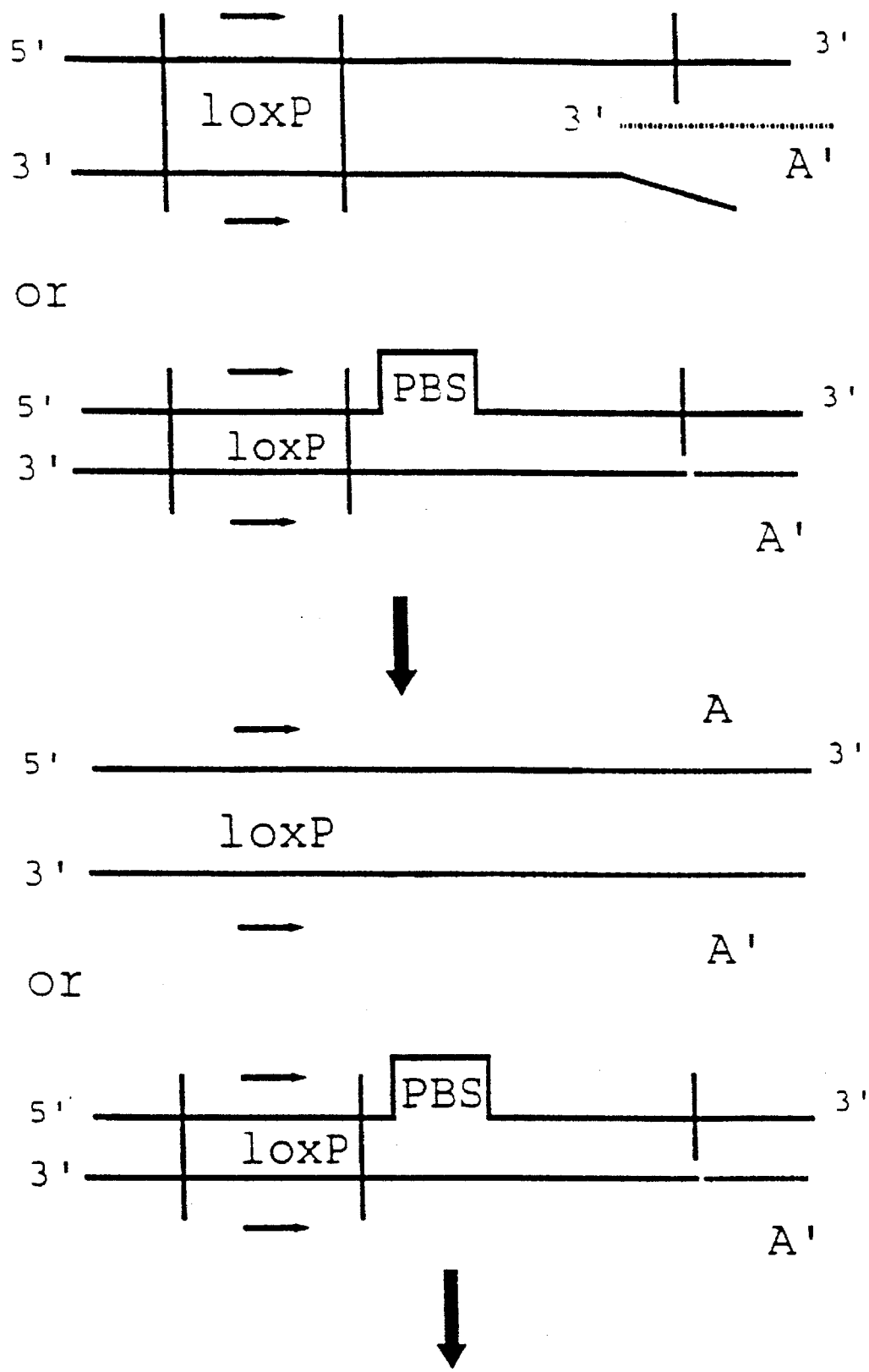
Figure 4C:
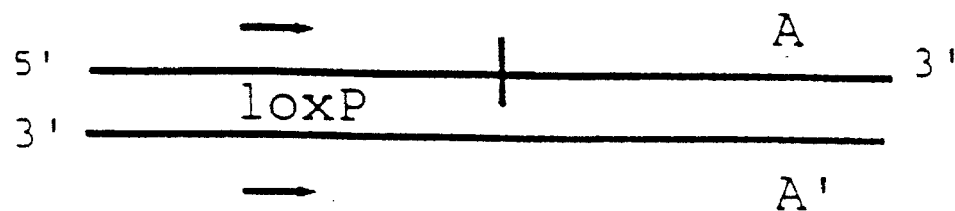
Figure 4C:
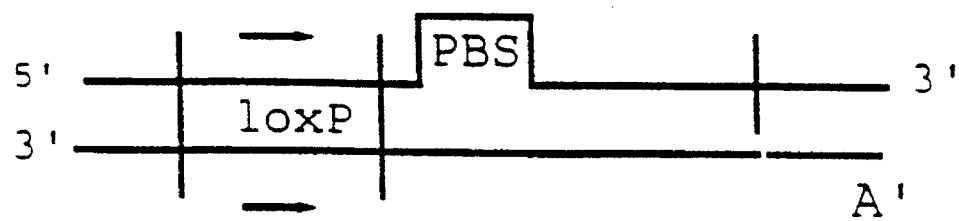
Figure 4C:
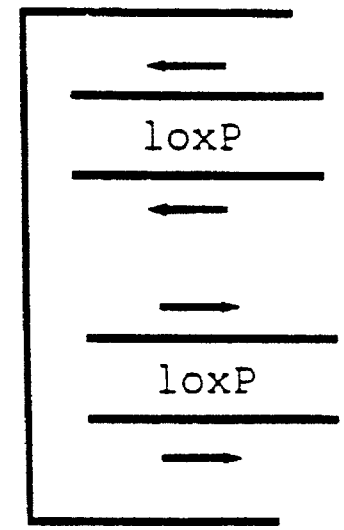
Figure 4C:
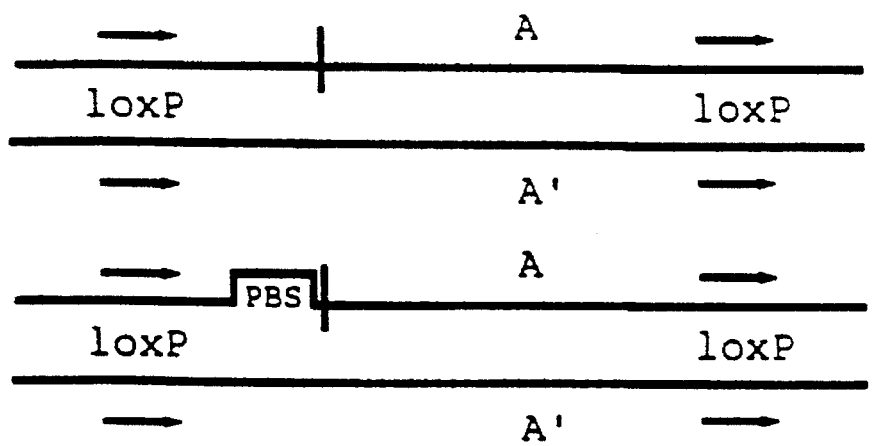
Figure 4D:
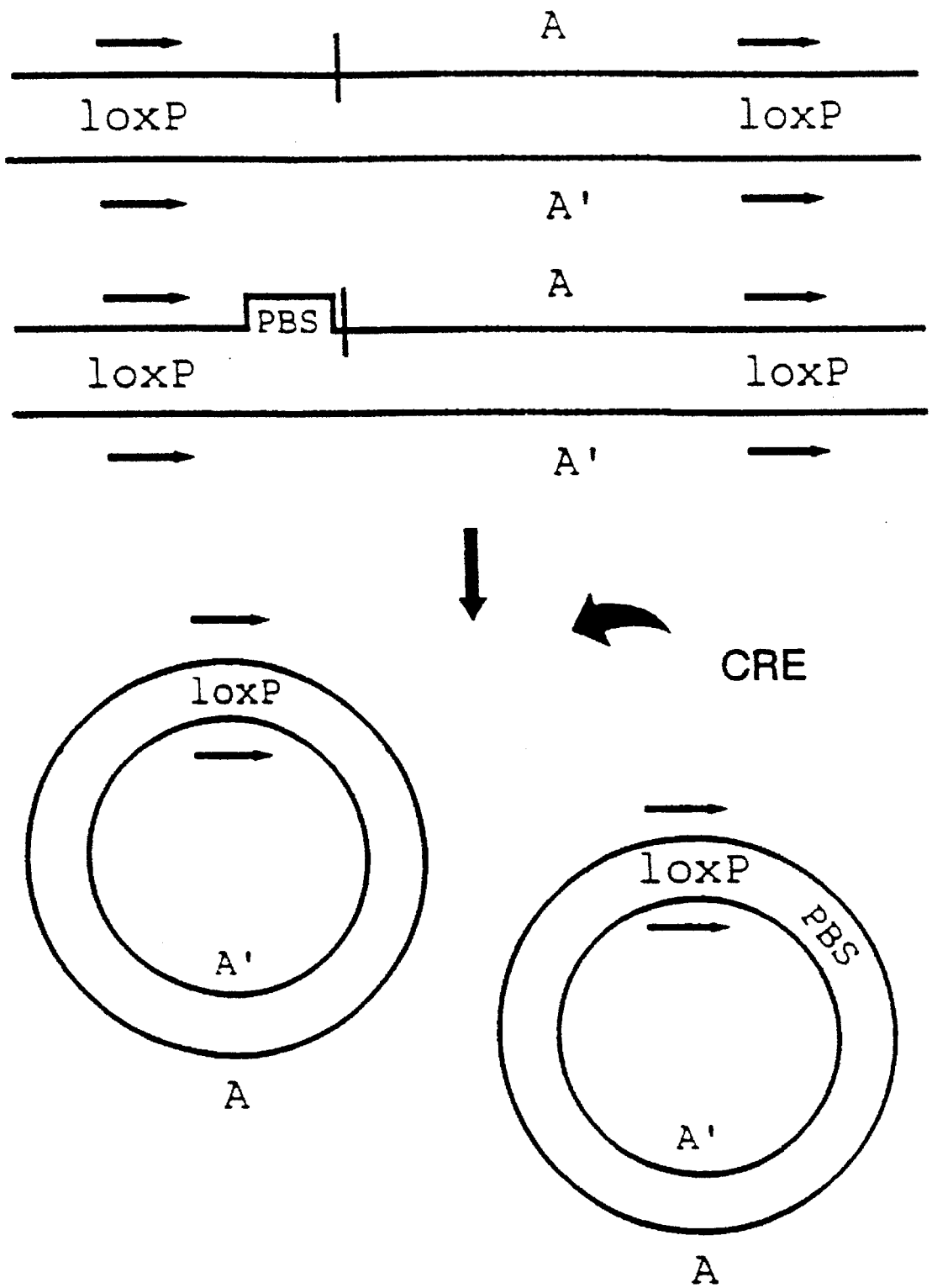

In a second subembodiment, to be used for example when the partially single-stranded/partially double-stranded 3' adaptor molecule(s) of the present invention is employed, the adaptation of the 3' terminus of the primer extension product is accomplished by the ligation of the primer extension molecule to the 3' adaptor molecule (FIG. 3B, line D). Because of the complementarity between the sequence of the protruding 3' terminus of the adaptor molecule and the 5' terminus of the primer extension molecule, the two molecules can hybridize to one another. Since the primer extension reaction has been controlled so that the average extension product terminates at a length corresponding to the end of the third region of the desired molecule, the average primer extension product will have a 5' terminus that can hybridize to the adaptor molecule.

In an alternative embodiment, of the invention, as for example when the concentration of the desired molecule is anticipated to be high, the molecules of the sample need not be denatured and can be directly cleaved into double-stranded molecules and then incubated with double-stranded or "hairpin"-shaped adaptors that contain recombinational sites and the other adaptor attributes described herein, so as to produce double-stranded molecules that contain the desired 3' and 5' adaptations.

When the adaptor molecule is DNA, any DNA ligase may be used to accomplish the ligation of the strands. Significantly, primer extension products that are longer or shorter than the precise length needed to permit the recessed 5' terminus of the adaptor to abut the 3' terminus of the primer extension are not amplified by the methods of the invention. They need not be removed from the reaction, and do not interfere with the subsequent desired amplification.

When the adaptor molecule is a DNA/RNA hybrid (in which the strand having the protruding 3' terminus is RNA), T4 ligase is employed to ligate the DNA strands together (Lehman, I. R., *Science* 186:790–797 (1974); Olivers, B. M. et al., *J. Molec. Biol.* 26:261 (1968); Kleppe, K. et al., *Proc. Natl. Acad. Sci.* (U.S.A.) 67:68 (1970); Fareed, G. C. et al., *J. Biol. Chem.* 246:925 (1971); Sgaramella, V. et al., *Proc. Natl. Acad. Sci.* (U.S.A.) 67:1468 (1970)).

The primer molecules will also have been modified to contain a recombinational site at their 5' terminus as discussed above. Such modification may be performed prior to or after the primer extension of the first or second steps of the method. If the modification is performed by ligation using a single-stranded molecule, the modification is performed prior to the third step of the process. If the modification is performed by ligation using a double-stranded molecule, the modification is performed after the 5' terminus of the primer extension product has been rendered double-stranded.

3. The Third Step of the Embodiment: Adaptation of the 5' Terminus of the Primer Extension Product Where the 5' terminus of the above-described primer was not initially modified to contain a DNA sequence that, when present in a double-stranded form comprises a recombinational site, such a sequence or site is added to the molecule produced after modification by the above-described 3' adaptor molecules.

a) The Methods Wherein the 3' Adaptor Molecule Comprises a Recombinational Site

In the subembodiment wherein the 3' adaptor molecule comprises a recombinational site, it is important that the orientation of that site be the same as the orientation of the recombinational site that is to adapt, or has adapted, the 5' terminus of the primer or primer extension product.

In this embodiment of the methods of the invention, illustrated in FIGS. 4A, 4B, 4C and 4D, the single-stranded adaptor molecule (if that 3' terminus adaptor molecule was used), or the strand of the above-described partially single-stranded and partially double-stranded adaptor molecule that possesses the protruding 3' terminus (if that 3' terminus adaptor molecule was used) is not removed, and is extended by a DNA polymerase to form a double stranded linear DNA molecule having termini that comprise recombinational sites (in direct orientation, if loxP sites). Preferably, the use of a primer binding site in the adaptor molecule will create a "bubble" of single-stranded region located between the recombinational sites.

Action by a recombinase on the recombinational sites yields a double-stranded circular molecule. If the molecule contains the described primer binding site, then such site will provide a single-stranded region which may be used to initiate the replication of the circular molecule.

Figure 5:
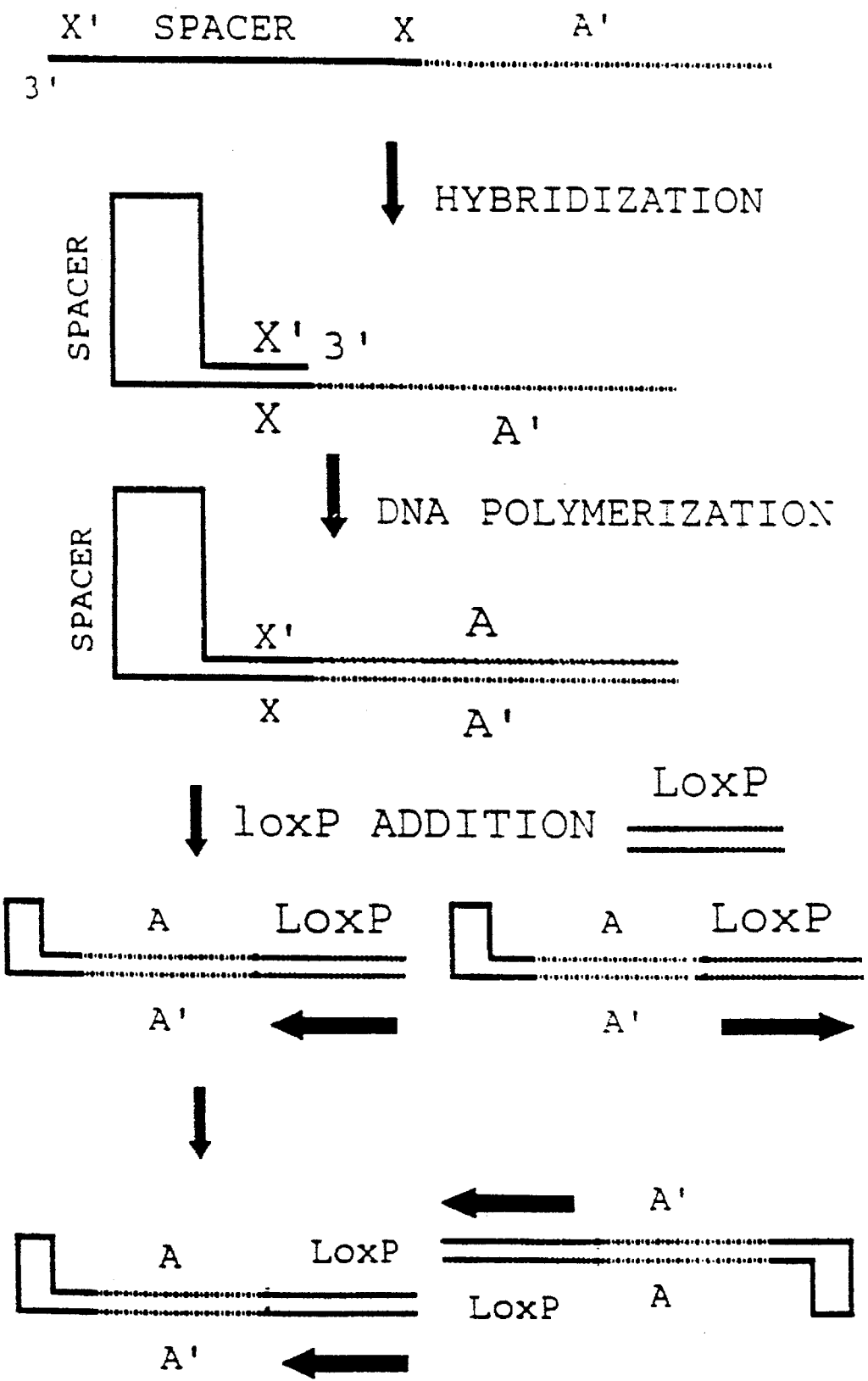
FIG. 5 shows the formation of hairpin loop molecules from the adaptation of the primer extension product with a 3' adaptor molecule having an inverted repeated sequence.

In one embodiment, such replication leads to a Q replicon. In a preferred embodiment, the double-stranded circle is "nicked" in one strand to permit a "rolling circle" replicon to form.

b) The Methods Wherein the 3' Adaptor Molecule Comprises an Inverted Repeated Sequence In the subembodiment wherein the 3' adaptor molecule comprises an inverted repeated sequence (FIG. 5), the strand of the adaptor molecule that contained the "protruding 3' terminus" is separated from the primer extension strand. Any means known in the art may be used to accomplish such separation. Optionally, and preferably, the strand of the adaptor molecule that contained the "protruding 3' terminus" is removed from the sample. In a less preferred embodiment, the strand of the adaptor molecule that contained the "protruding 3' terminus" is labelled with biotin. In this subembodiment, the sample is heated to denature double-stranded molecules and treated with a biotin-binding agent (for example, streptavidin) to thereby separate or remove the biotinylated molecule from the primer extension product.

In the most preferred subembodiment, the strand of the adaptor molecule that contained the "protruding 3' terminus" is RNA, and is separated or removed from primer extension product through the enzymatic activity of RNAse H, which preferentially degrades the RNA strand of an RNA/DNA hybrid.

The reaction conditions are then adjusted, if necessary, to permit DNA polymerization to occur. DNA polymerase is added, if needed, to the reaction, along with nucleotide triphosphates, etc., such that template-dependent extension of the 3' terminus of the adapted molecules can occur.

Since the adaptor molecule contains an inverted repeat, such polymerization results in the formation of a hairpin loop structure. In a preferred mode of the invention, the adaptation of the 5' terminus of the extension product is accomplished after such hairpin loop structures have formed, by providing double-stranded recombinational sites to the reaction, and permitting such sites to ligate to the terminus of the hairpin. This mode of adaptation is preferred, since the ligation of such molecules will occur in a randomized orientation, such that, on average one-half of the molecules will contain recombinational sites that are in one orientation, and one-half of the molecules will contain recombinational sites that are in the opposite orientation.

Figure 6:
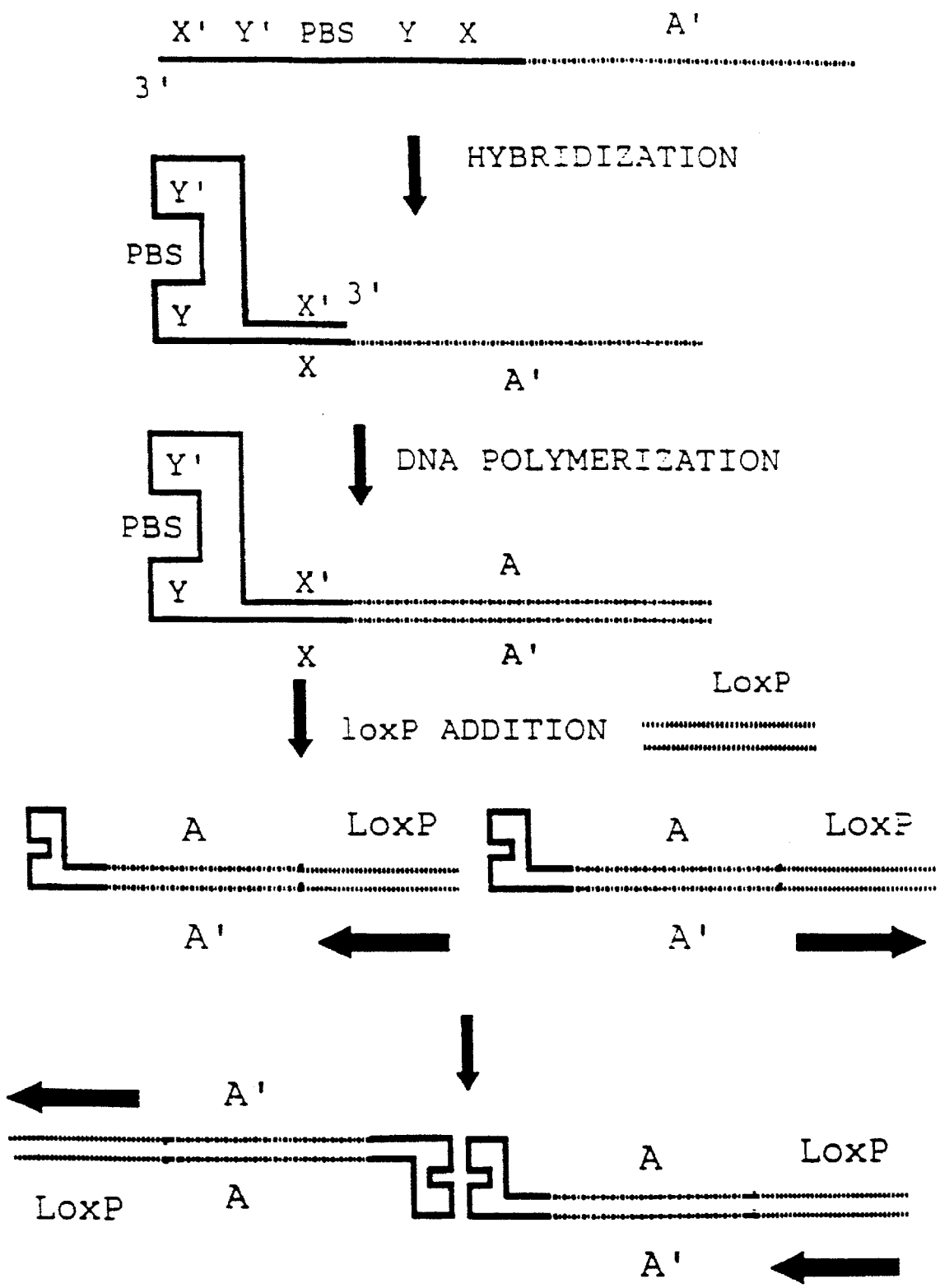
FIG. 6 shows the formation of "bow-tie" molecules from the adaptation of the primer extension product with a 3' adaptor molecule having a pair of nested inverted repeated sequences.

Action by a recombinase on the recombinational sites of two adapted hairpin loop molecules having the opposite orientation (i.e. direct repeat) yields a single-stranded circular molecule. If the molecule contains the described primer binding site, then such site will provide a region which may be used to initiate the replication of the circle in a twin origin "rolling circle" replicon manner as described below.

c) The Methods Wherein the 3' Adaptor Molecule Comprises a Pair of Nested Inverted Repeated Sequences In the subembodiment wherein the 3' adaptor molecule comprises a pair of nested inverted repeated sequences (FIG. 6), the strand of the adaptor molecule that contained the "protruding 3' terminus" is separated from the primer extension strand, in the manner described above.

The reaction conditions are then adjusted, if necessary, to permit DNA hybridization to occur. The random hybridization of the primer extension products will also result in the formation of a double-stranded molecule having different external inverted repeated sequences (i.e. formed from different 3' adaptor molecules, having different external inverted repeated sequences such as are depicted as X/X' and Q/Q'). The strands of these molecules will anneal to one another due to hybridization between their respective internal inverted repeated sequences. Because the external inverted repeated sequences of the two strands are not complementary to one another, they will not hybridize to one another. Thus, the external repeated sequences of each strand will be able to participate in intra-strand hybridization.

After permitting such hybridization, DNA polymerase is added, if needed, to the reaction, along with nucleotide triphosphates, etc., such that template dependent extension of the 3' terminus of the adapted molecules can occur. The action of DNA polymerase on these molecules will lead to the formation of a "bow-tie" molecule characterized in possessing two hairpin loops that are annealed to one another by virtue of the hybridization between the internal inverted repeated sequences of the molecules.

The terminus of these molecules is then preferably adapted by providing double-stranded recombinational sites to the reaction, and permitting such sites to ligate to the terminus of the hairpin, in the manner described above. Approximately one-half of all bow-tie molecules will contain recombinational sites in direct repeat.

Action by a recombinase on the recombinational sites of two adapted hairpin loop molecules having the opposite orientation (i.e. direct repeat) yields a single-stranded circular molecule. If the molecule contains the described primer binding site, then such site will provide a region which may be used to initiate the replication of the circle in a twin-origin "rolling circle" manner as described below.

4. The Fourth Step of the Embodiment: Amplification

Because the above steps produce molecules that contain recombinational sites (e.g. loxP), the addition of a recombinase (preferably Cre) catalyzes a double-strand exchange at the recombinational sites of the molecules.

Figure 7:
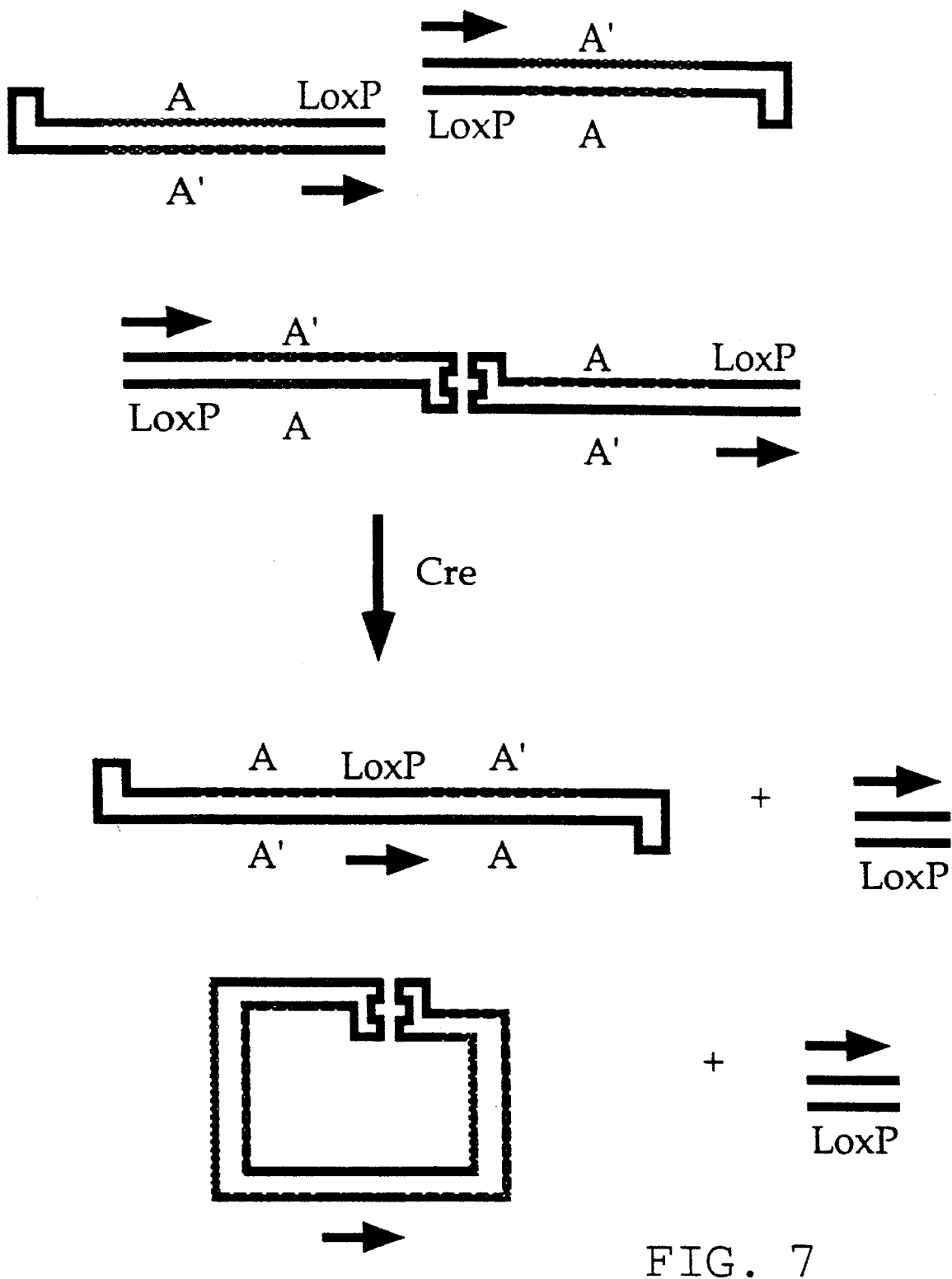
FIG. 7 shows the conversion of hairpin loop and "bow-tie" molecules having directly repeated recombinational sites into single strand circular molecules.

For a "bow-tie" molecule having recombinational sites in the same directional orientation, the recombinational action of the recombinase converts the linear molecules into a single strand circular molecule (FIG. 7). Similarly, two hairpin loops having recombinational sites in the same directional orientation can be recombined to form a single strand circular molecule (FIG. 7). These circular molecules are characterized in having two copies of each strand of the desired sequence, four copies of the spacer region (which optionally comprises the described internal inverted repeated sequences), two copies of each of the two external inverted repeated sequences and a single recombinational site (FIG. 7).

Unless the initially employed primer have been sequences removed or destroyed, these sequences will hybridized displace the strands of the circular molecule. Such displacement may be facilitated by thermally denaturing the molecule, if desired. Such sequences may be used to amplify the desired sequence.

Alternatively, amplification may be accomplished by providing a primer that is complementary to the optional primer binding site. Since the circular molecule does not contain any sequence complementary to the primer binding site, such primer molecules can readily access the site and initiate amplification without thermal denaturation.

Figure 8A:
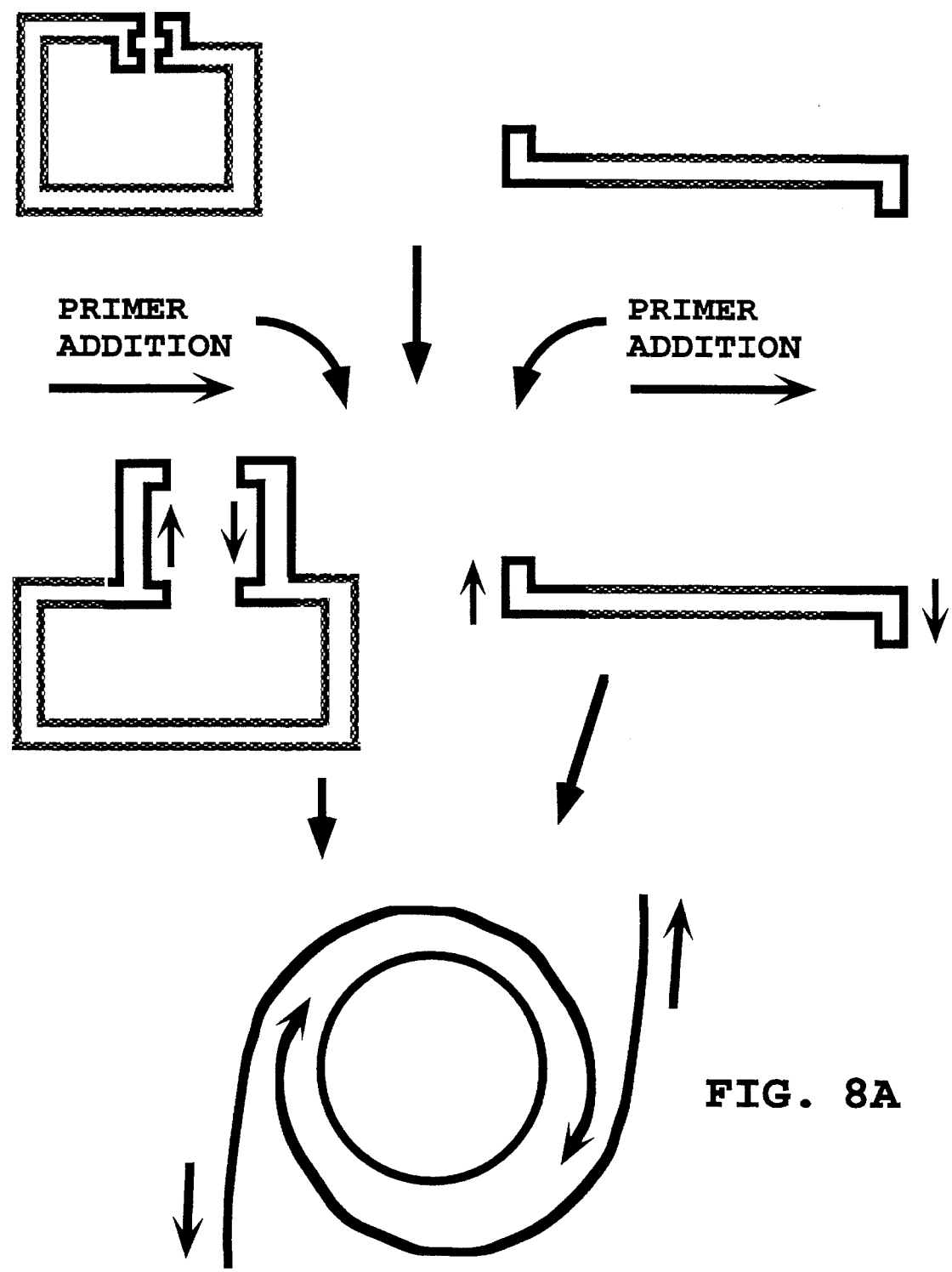
FIGS. 8A and 8B show the amplification replicons of the present invention.

For single-stranded circular molecules, since the primers can anneal at two sites on the molecule, primer extension yields a twin-origin "rolling circle" replicon (i.e. a rolling circle replicon having two extending strands, as shown in FIG. 8A).

Figure 8B:
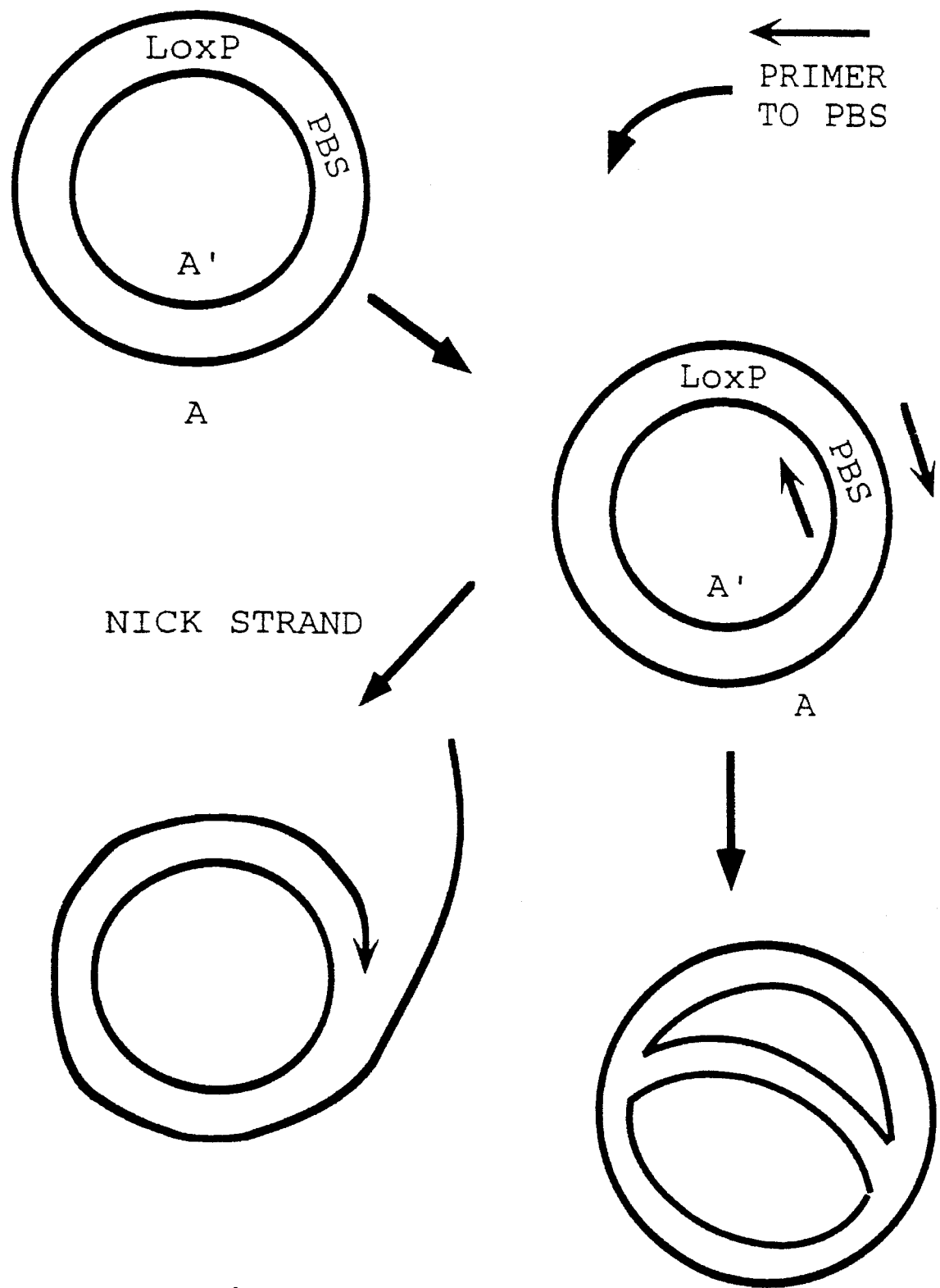

For the double-stranded circular molecules produced by the above method steps, amplification can be preferably obtained in either of two manners. In one embodiment, in which the addition of topoisomerase or gyrase is desirable, the double-stranded molecule is replicated to form a Q replicon (FIG. 8B). More preferably, one strand of the double-stranded molecule is nicked, such that primer extension results in the displacement of the nicked strand and the formation of a "rolling circle" replicon. Such nicks can be produced by radiation, by chemical adducts (ethidium bromide, etc.), by an endonuclease, or by other means. A preferred method for forming such nicks is by incorporating at least one modified nucleotide (e.g., a5'-[a-thio]triphosphate (Pharmacia) or methylated nucleotide) into one strand of a restriction site (preferably present in the 3' adaptor molecule). Cleavage at that site by the relevant restriction endonuclease will create a single-strand nick (Walker, G. T. et al., *Proc. Natl. Acad. Sci.* (U.S.A.) 89:392–396 (1992)).

As each strand of any of the above replicons is extended, it provides additional template binding sites for additional primer extension. Thus, the kinetics of amplification are similar to, but faster than, viral burst kinetics.

The presence of inverted repeated sequences and recombinational sites permits additional hairpin loop structures to form. Since the reaction contains Cre, it will mediate recombination between such additional hairpin loop structures to form additional circular structures, thus increasing the number of amplification foci in the reaction.

All of the enzymes used in this amplification reaction may be active under the same reaction conditions. Indeed, buffers exist in which all enzymes are near their optimal reaction conditions. Therefore, the amplification process of the present invention can be done in a single reaction volume without any change of conditions such as the replacement of reactants. Thus, though this process has several steps at a molecular level, operationally it may have a single step. Once the reactants are mixed together, one need not add anything or change conditions, e.g. temperature, until the amplification reaction has exhausted one or more components. During this time, the nucleic acid sequence being amplified will have been increased many-fold.

B. Ligation Extension Method

In an alternate embodiment, the nucleic acid of the sample is cleaved (either enzymatically, or by physical means, such as shearing, sonication, etc.) into linear double-stranded polynucleotides. The ends of the polynucleotides are adapted (if necessary) so as to permit the polynucleotide to be inserted (most preferably via ligation) into a target restriction endonuclease cleavage site of either a precursor linear double-stranded molecule, or into a precursor circular molecule. In a preferred embodiment of such methods, the ligase will not be thermally stable, or will be otherwise labile, such that after the initial ligation reaction the ligase can be substantially inactivated.

1. Forming the Desired Circular Molecule a) Precursor Linear Molecule Method In this subembodiment of the present methods, the target polynucleotide is introduced (via ligation, preferably at a restriction site) into the above-described linear precursor molecule. Such introduction forms a double-stranded DNA molecule that comprises: (a) a first lox site located at a first end of the linear molecule, (b) a second lox site located at a second end of the linear molecule, wherein the first and the second lox sites are directly oriented with respect to one another so as to permit the Cre to mediate the circularization of the linear double-stranded molecules, and to thereby form the double-stranded circular molecule; (c) the target polynucleotide region located internal to the first and second lox sites; and (d) a hemi-modified restriction site located between the target polynucleotide region and one of the lox sites, wherein one strand of the hemi-modified restriction site of each of the linear molecules contains modified nucleotides (especially methylated nucleotides and (α-thio-)phosphorothioate nucleotides), such that a restriction endonuclease that recognizes such restriction site will be incapable of cleaving that strand containing the modified nucleotides.

In accordance with the present invention, such a molecule is then incubated in the presence of Cre under conditions sufficient to permit circularization of the molecule such that a circular molecule b. Precursor Circular Molecule Method This subembodiment is similar to the above-described precursor linear molecule method, except that the step of the initial circularization is rendered unnecessary because the molecules are initially circularized.

Thus, in this subembodiment, the target polynucleotide is introduced (via ligation) into the target restriction site of the above-described circular precursor molecule. The resulting circular molecule comprises: (a) a lox site; (b) the target polynucleotide; and (c) a hemi-modified restriction site located between the target restriction endonuclease cleavage site and the lox site.

2. Amplification of the Circular Molecule

This circular molecule is then incubated in the presence of a restriction endonuclease that recognizes the hemi-modified site and causes a single-strand nick or gap having a 3' hydroxyl terminus to be created.

A polymerase and nucleotides are added to the reaction (if not already present). Under such conditions, the polymerase will mediate the extension of the created 3' terminus, and the consequent strand displacement of the 5' terminus of the cut strand. Such primer extension recreates the hemi-modified restriction site, which is then cut, generating a new extendible 3' terminus. The net effect of such primer extension, strand displacement and nicking reactions is the displacement of a linear single-stranded molecule having a lox site at (or near) its 5' terminus and a region complimentary to the single primer at its 3' terminus.

The single primer is added (if not already present in the reaction). The presence of the single primer (and the polymerase and nucleotides) permits the linear molecule and the single primer to act as templates for one another to recreate the initially formed double-stranded DNA molecule.

Significantly, the above reactions use a single primer to mediate the amplification of a specific target polynucleotide even if that molecule were initially present in a complex mixture of undesired polynucleotides.

C. Isolation or Purification of the Amplified Molecules

This invention may be combined with many other processes in the arts of molecular biology to achieve a specific end. Of particular interest is purifying the target sequence from the other sequences in the nucleic acid sample. This can be accomplished most advantageously by annealing the nucleic acid sample to an oligonucleotide that is complementary to the target and is immobilized on a solid support. A convenient support would be a micro-bead, especially a magnetic micro-bead. After being so bound, the non-target sequences could be washed away, resulting in a complete or a partial purification.

After an amplification is performed, one may wish to detect any amplification products produced. Any number of techniques known to the art may be adapted to this end without undue experimentation. Particularly advantageous in some situations is the capture of RNA amplification products by a DNA oligonucleotide complementary to an RNA sequence determined by the target sequence, the oligonucleotide being bound to a solid support such as a magnetic micro-bead. Preferably, this oligonucleotide's sequence does not overlap with that of any oligonucleotide used to purify the target before the amplification. RNA:DNA hybrids thus formed may then be detected by antibodies that bind RNA:DNA heteroduplexes. Detection of the binding of such antibodies can be done by a number of methods well known to the art.

Alternatively, amplified nucleic acid can be detected by gel electrophoresis, hybridization, or a combination of the two, as is well understood in the art. Since the molecules that are being amplified comprise both strands of the desired sequence, the use of restriction endonucleases can cleave the reaction products into discrete and defined fragments. Those in the art will find that the present invention can be adapted to incorporate many detection schemes.

Sequences amplified according to the methods of the invention may be purified (for example, by gel electrophoresis, by column chromatography, by affinity chromatography, by hybridization, etc.) and the fractions containing the purified products may be subjected to further amplification in accordance with the methods of the invention.

The present invention includes articles of manufacture, such as "kits." In one embodiment, such kits will, typically, be specially adapted to contain in close compartmentalization a first container which contains a nucleic acid molecule comprising a recombinational site at its 5' terminus and a region complementary to the desired polynucleotide at its 3' terminus, and a second container which contains a nucleic acid molecule comprising a recombinational site at its 5' terminus and a region having a sequence complementary to the 5' terminus of the desired polynucleotide at its 3' terminus, and, optionally, a third containing a recombinase suitable for catalyzing the recombination of the sequence of the first container which. The kit may also, optionally, contain one or more DNA and/or RNA polymerases, ligase, buffers, etc. in amounts sufficient to permit the amplification of a desired nucleic acid molecule. The kit may additionally contain instructional brochures, and the like.

Having now generally described the invention, the same will be more readily understood through reference to the following examples which are provided by way of illustration, and are not intended to be limiting of the present invention, unless specified.

Example 1

Isothermal Amplification Method I

Figure 9:
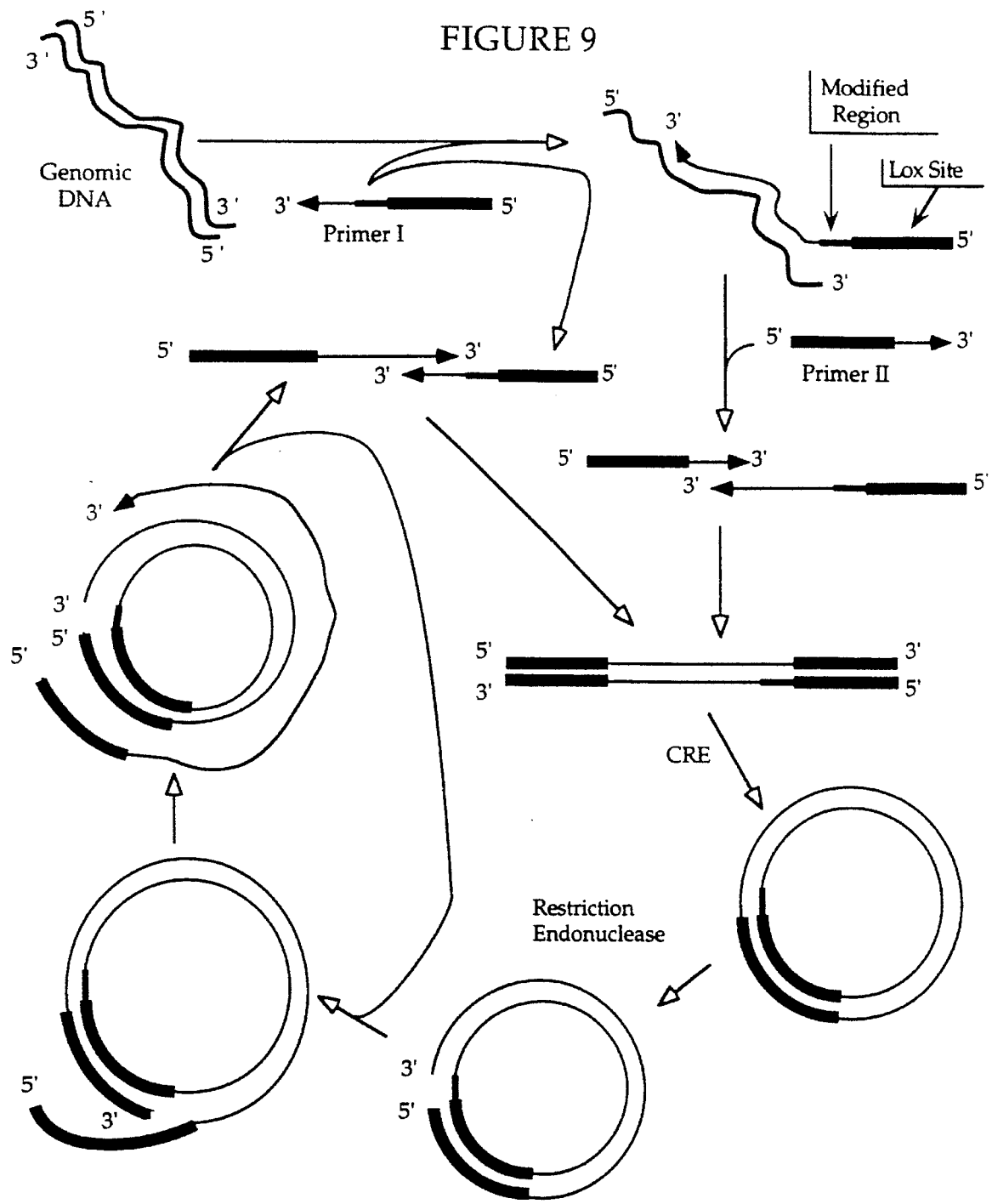
FIG. 9 provides a diagramatic representation of an illustrative isothermal amplification reaction described in Example 1.

FIG. 9 provides a diagrammatic representation of a first preferred method for achieving the amplification of a desired region of genomic DNA.

With reference to FIG. 9, a sample of double-stranded genomic DNA is denatured, as by heat, etc., and incubated in the presence of a "first" primer molecule whose 3' terminus is complementary to a target polynucleotide region whose amplification is desired.

In the preferred embodiment shown in FIG. 9, the "first" primer comprises three polynucleotide regions: (1) a "target complement" polynucleotide region (i.e., a polynucleotide complementary to a polynucleotide present at the 3' end of the target polynucleotide that is to be amplified), (2) a polynucleotide region containing modified nucleotides and (3) a "proto-lox" polynucleotide region (i.e., a polynucleotide, which, if hybridized to a complementary polynucleotide would form a double-stranded molecule that would comprise a lox site. The polynucleotide region containing modified nucleotides is located 3' to the "proto-lox" region. The sequence of the polynucleotide region containing modified nucleotides is selected such that if it were hybridized to a complementary polynucleotide, the resulting double-stranded polynucleotide would comprise one or more restriction endonuclease recognition site(s). The sequence of the polynucleotide region containing modified nucleotides of the primer is preferably further selected such that this restriction endonuclease recognition site is recognized by a restriction endonuclease that is capable of cleaving DNA that lacks such modified nucleotides, but is substantially or completely incapable of cleaving a polynucleotide containing such modified nucleotides. Examples of modified nucleotides include ribonucleotides (where the polynucleotides are DNA), phosphorothioate nucleotides, methylated nucleotides, bromodeoxyuridine, deoxyuridine, etc. Examples of suitable restriction endonucleases and their recognition sequences are described in Sambrook, J., et al. (In: *Molecular Cloning, A Laboratory Manual*, Second Edition, Cold Spring Harbor Laboratories, Cold Spring Harbor, N.Y. (1989)), in Walker, G. T. et al. (*Proc. Natl. Acad. Sci.* (U.S.A.) 89:392–396 (1992)), and in the GibcoBRL/Life Technologies 1993–1994 Catalog and Reference Guide, all of which references are herein incorporated by reference.

The primer is incubated with the denatured DNA of the sample under conditions which permit both hybridization and template dependent primer extension to occur. Thus, a polymerase and (non-modified) nucleotides are provided to the reaction. The primer extension reaction is terminated by adjusting the reaction conditions to cause the denaturation of the extended primer from its template molecule.

A "second" primer is introduced into the reaction. Although, in a preferred embodiment, this second primer is introduced after the termination of the primer extension reaction, such second primer may be introduced at any time before, during or after the introduction of the modified first primer discussed above. The second primer comprises two polynucleotide regions: (1) a "target" polynucleotide region present at the 5' end of the polynucleotide that is to be amplified, and (2) a "proto-lox" polynucleotide region. The "proto-lox" region is located 5' to the "target" region of the primer.

As will be appreciated, if the target molecule was present in the initial sample, the extension product of the first primer molecule will contain a region that is complementary to the 3' terminus of the second primer (see FIG. 9). Thus, the reaction conditions are adjusted to permit hybridization and primer extension to occur. As a consequence of the presence of polymerase and nucleotides, the annealed first and second primers produce blunt-ended linear molecules in which the desired "target" region is flanked by lox sites. Significantly, the orientation of the "proto-lox" polynucleotides of the first and second primers are oriented (with respect to the target complement and target polynucleotide regions) such that the flanking lox sites are in a direct repeated orientation.

Cre recombinase is added to the reaction. As will be appreciated, Cre may be added at an earlier step in the process if desired. The presence of Cre catalyzes the circularization of the lox sites of the blunt-ended linear molecules produced above. As a result, a double-stranded circular molecule is formed. The double-stranded molecule contains the target polynucleotide, a single lox site, and a restriction endonuclease site in which one strand (i.e., the strand derived from the first primer) contains modified nucelotides and the other strand (i.e., that derived from the extension of the second primer via DNA polymerase) does not contain modified nucleotides.

A restriction endonuclease that recognizes the restriction endonuclease recognition site of the double-stranded circular molecule is added to the reaction. As discussed above, the restriction endonuclease and the recognition site are selected such that the endonuclease does not cleave DNA containing modified nucelotides. Thus, the introduction of the endonuclease "nicks" (if a single site is present) or "gaps" (if more than one site are present) the non-modified strand of the circular molecule.

Such "nicking" or "gapping" creates a 3' terminus which may be extended by the previously added polymerase. Such extension displaces the 5' terminus of the non-modified strand. As the polymerase extends the 3' terminus through the region containing the restriction site, a new hemi-modified site is created. This new site is "nicked" or "gapped" by the previously added restriction endonuclease, and thus generates yet another 3' terminus that may be extended by the polymerase (see, FIG. 9). Since the cleavage that creates this subsequent 3' terminus occurs behind the initially created 3' terminus, it does not affect the ability of a polymerase to extend the initially created 3' terminus. In a like manner, the reactions continue without further intervention: generating a new 3' terminus, extending that terminus, creating a new hemi-modified restriction site, "nicking" or "gapping that site to create yet another 3' terminus.

As each primer extension product is extended, it displaces the prior strand that was hybridized to its template. This strand displacement reaction continues without further intervention, and generates a set of identical linear molecules, all of which contain a "proto-lox" site and the target polynucleotide region.

At this point in the protocol, a linear isothermal amplification of one strand of the target polynucleotide has been accomplished. Since the "first" primer (discussed above) has not been removed from the reaction, it will hybridize with the linear amplification product, and thereby provide a substrate for a new primer extension reaction. The consequence of this reaction is the generation of a new double-stranded blunt-ended linear molecule in which a double-stranded target region is flanked by lox sites (see, FIG. 9). This new blunt-ended molecule is identical to that described above.

Since the reaction still contains Cre recombinase, the linear molecule is converted into the above-described double-stranded circular molecule. Significantly, the newly formed circular molecule contains the same hemi-modified restriction endonuclease recognition site as the initially formed circular molecules. Thus, cleavage of that site results in a "nick" or "gap," which creates a further amplification nucleus.

In sum, an exponential isothermal reaction results. This reaction produces double-stranded polynucleotides having the sequence of the desired target molecule.

Significantly, if the "first" primer were provided in limiting amounts, were made of RNA and degraded (as with RNase A, etc.) after the reaction had been initiated, or if it contained other nuclease sensitive bases, or was at least partially biotinylated, it would be possible to exhaust, degrade or remove the first primer from the reaction after the reaction had initiated. Upon such exhaustion, degradation or removal, the reaction will shift from an exponential amplification reaction that amplifies both strands of the target to a linear reaction that amplifies only one stand of the target molecule. Such a modification is desirable in instances in which the purification and recovery of only a single strand is desired (e.g., in DNA sequencing, and in probe generation).

Figure 10:
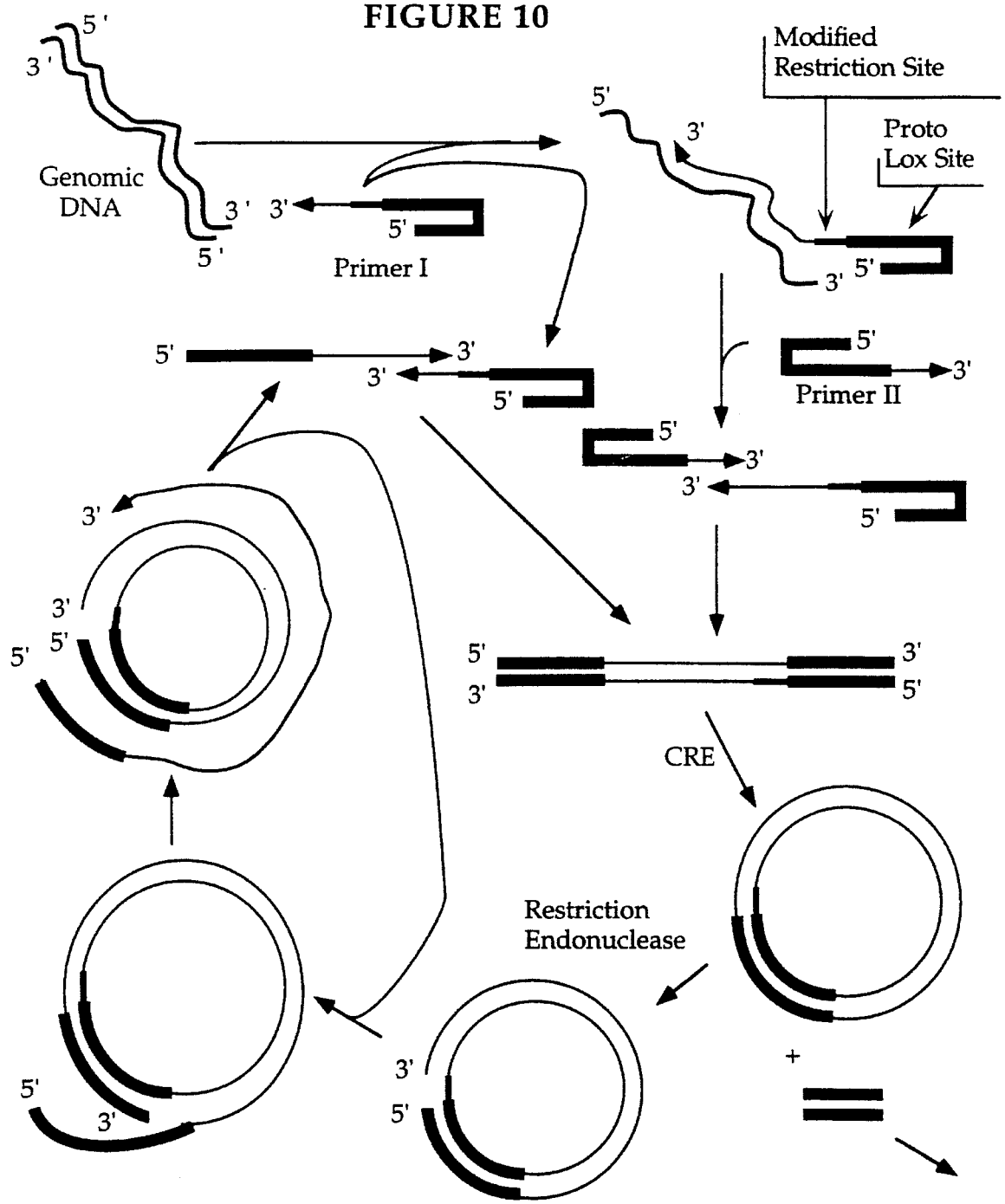
FIG. 10 provides a diagramatic representation of an alternative illustrative isothermal amplification reaction described in Example 1.

FIG. 10 provides an alternative embodiment of the above-described method. In this alternative embodiment, either or both of the first and second primers is modified to contain a sequence that causes the 5' terminus of the primer(s) to partially self-hybridize to the primer, such that the 3' terminus of the primer is single-stranded. Such self-hybridization acts to minimize or prevent any hybridization between the first and second primer molecules.

Example 2

Isothermal Amplification Method II

Figure 13:
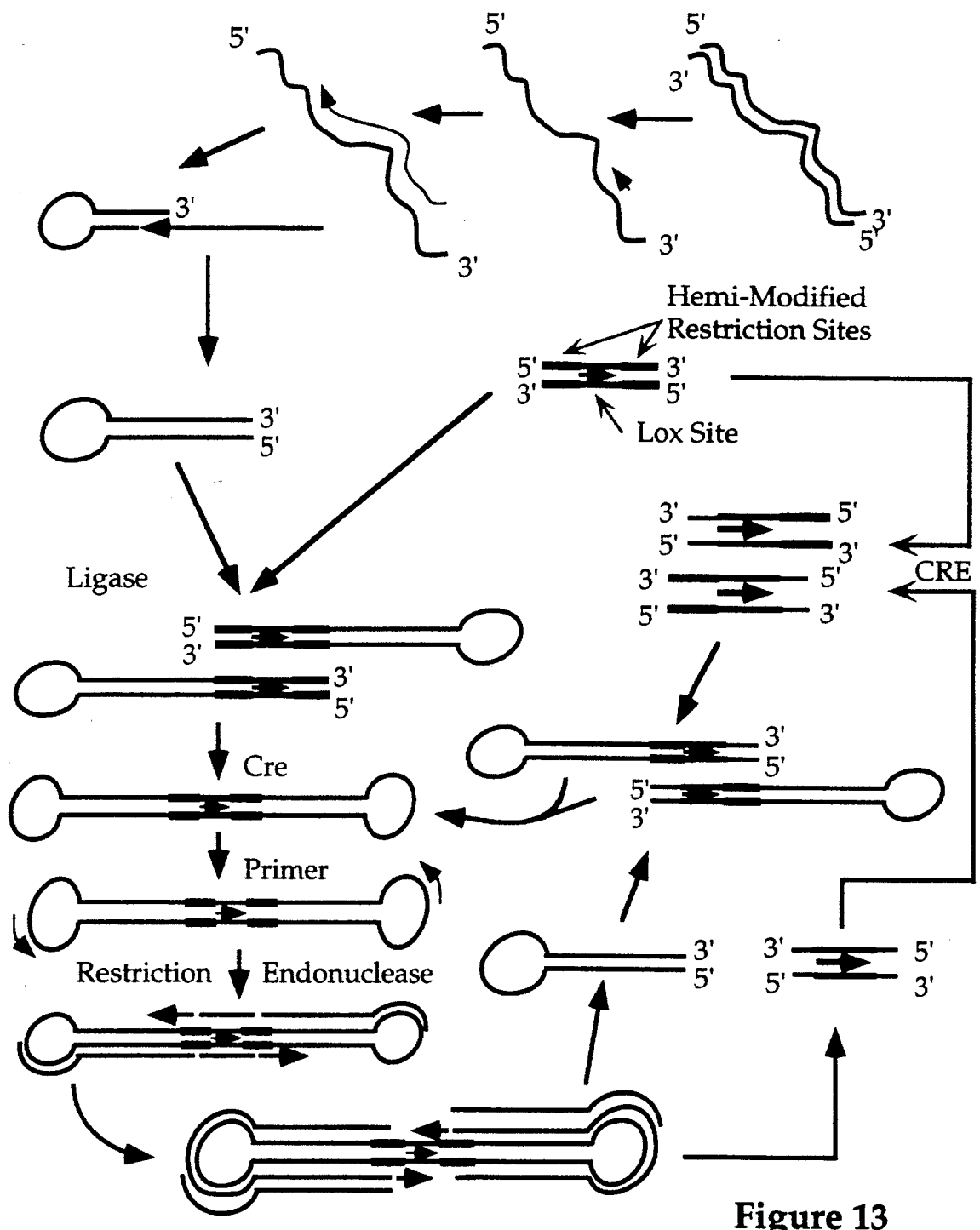
FIG. 13 provides a diagramatic representation of an illustrative isothermal amplification reaction described in Example 2 in which an unmodified primer is used and a DNA ligase is employed.

FIG. 13 provides a diagrammatic representation of a second preferred method for achieving the amplification of a desired region of genomic DNA.

With reference to FIG. 13, a sample of double-stranded genomic DNA is denatured, as by heat, etc., and incubated in the presence of a "first" primer molecule whose 3' terminus is complementary to a target polynucleotide region whose amplification is desired.

In the preferred embodiment shown in FIG. 13, the "first" primer need not be modified in any respect. It merely needs to be of sufficient length to permit stable hybridization.

The primer is incubated with the denatured DNA of the sample under conditions which permit both hybridization and template dependent primer extension to occur. Thus, a polymerase and (non-modified) nucleotides are provided to the reaction. The primer extension reaction is terminated by modifying the reaction conditions to cause the denaturation of the extended primer from its template molecule.

A second primer is added to the reaction. Although, in a preferred embodiment, this second primer is introduced after the termination of the primer extension reaction, such second primer may be introduced at any time before, during or after the introduction of the modified first primer discussed above. The second primer comprises a partially single-stranded-partially double-stranded "loop" structure. It contains a protruding 3' terminus whose sequence is the same as a sequence present at the 5' end of the polynucleotide that is to be amplified, such that the protruding 3' terminus is complementary to the 3' terminus of the extension product of the first primer.

The reaction conditions are adjusted to permit both the ligation of the primer extension product of the first primer to the recessed 5' terminus of the second primer, and the template dependent extension of the protruding 3' terminus of the second primer. Thus ligase, polymerase and nucleotides are provided. The resulting product comprises a double-stranded, blunt-ended, target molecule having the 5' terminus of one strand connected to the 3' terminus of the other via the "loop" structure of the second primer (see, FIG. 13).

A linker molecule is introduced into the reaction. The linker molecule is a blunt-ended, double-stranded linear molecule which comprises a lox site flanked by one or more pairs of restriction endonuclease recognition sites. Preferably, as shown in FIG. 13, the restriction sites are composed of modified nucleotides. Both strands of the restriction site are modified.

The previously added ligase catalyzes the ligation of the linker molecule to the free 3/5' terminus of the previously formed product (FIG. 13) to form a "looped target molecule." Such ligation can occur in either of two possible orientations (owing to the directionality of the lox site). The orientation of ligation is unimportant to the reaction.

Two products of such ligation in which the lox site has been ligated in opposite orientations can be recombined via the addition of Cre to form an end-looped structure having two copies of the double-stranded target polynucleotide separated by a single lox site.

A third primer is introduced which is preferably complementary to a polynucleotide region of the non-base paired "loop" part of the molecule. The previously added polymerase, causes the 3' terminus of this third primer to be extended around the "loop" and into the polynucleotide region of the target, displacing the hybridized non-template strand. The third primer is optional, and added to facilitate the initiation of the amplification reaction. Its presence is not needed during amplification.

Extension of the primer past the modified restriction site, creates a hemi-modified restriction site. The introduction into the reaction of a restriction endonuclease that recognizes this site, causes a "nick" or "gap" in the non-modified strand. As in Example 1, once started, these reactions continue without further intervention. Thus, primer extension creates a hemi-modified site, that site is cleaved by a restriction endonuclease thereby creating a new 3' terminus which is extended to form a new hemi-modified site, thereby restarting the cycle.

Again, as in Example 1, the cleavage that creates a new 3' terminus occurs behind a previously created 3' terminus, and thus does not affect the ability of a polymerase to extend the initially created 3' terminus. As shown in FIG. 10, the product of such primer extension and cleavage reactions is the same "looped target molecule" as that described above.

Since the reaction still contains ligase and the linker molecules, such molecules will be ligated together, and the products of such ligation can then circularize via the action of the previously added Cre recombinase. Such circularization generates new amplification foci.

In sum, the method achieves the exponential amplification of both strands of the target polynucleotide without using modified primers.

The isothermal nature of the amplification processes described above permits each product of each reaction to proceed through the entire set of reactions at its own pace. This capacity, which reflects the isothermal nature of the reactions, is in marked contrast to cyclic reactions such as the polymerase chain reaction, in which all reactants are required to procede in unison to the next step of the reaction. By avoiding such a requirement, the isothermal amplification methods of the present invention provide faster reaction kinetics.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

What is claimed is:

1. A method for amplifying a target polynucleotide region of a double-stranded nucleic acid molecule present in a sample, which comprises the steps:

(A) incubating linear double-stranded nucleic acid molecules in the presence of a polymerase, nucleotides, a site-specific recombinase, a primer and a restriction endonuclease; wherein:

(i) each of said linear double-stranded nucleic acid molecules has two ends and comprises:

(a) a first recombinational site recognized as a substrate by said recombinase, located at a first end of said linear molecule;

(b) a second recombinational site recognized as a substrate by said recombinase, located at a second end of said linear molecule, wherein said first and said second recombinational sites are oriented with respect to one another so as to permit said recombinase to mediate the circularization of said linear double-stranded molecules, and to thereby form double-stranded circular molecules;

(c) said target polynucleotide region, located internal to said first and second recombinational sites; and (d) a hemi-modified restriction site, located between said target polynucleotide region and one of said recombinational sites, wherein one strand of said hemi-modified restriction site of each of said linear molecules contains at least one modified nucleotide residue;

(ii) said restriction endonuclease is substantially incapable of cleaving a strand of a nucleic acid molecule that contains said modified nucleotide residue;

(iii) said primer comprises from 3' terminus to 5' terminus:

(a) a first polynucleotide region complementary to a 3' terminal portion of said target polynucleotide region;

(b) a second polynucleotide region containing at least one of said modified nucleotide residues, wherein, if said second polynucleotide region were hybridized to a complementary polynucleotide, a double-stranded polynucleotide would thereby be formed that would contain one or more restriction endonuclease cleavage sites that would be recognized by said restriction endonuclease; and (c) a third polynucleotide region, wherein, if said third polynucleotide region were hybridized to a complementary polynucleotide, a double-stranded polynucleotide would thereby be formed that would contain a recombinational site recognized as a substrate by said recombinase; and (iv) said incubation is conducted under conditions suitable for permitting:

(a) said recombinase to circularize said linear double-stranded nucleic acid molecules and thereby form said double-stranded circular molecules;

(b) said restriction endonuclease to cleave one strand of said hemi-modified restriction endonuclease recognition site of said double-stranded circular molecule and thereby create an extendible 3' terminus;

(c) said polymerase and said nucleotides to mediate template dependent extension of said extendible 3' terminus and thereby cause displacement of a single-stranded polynucleotide containing said target polynucleotide region; said extension further resulting in the creation of a new hemi-modified restriction recognition site;

(d) said restriction endonuclease to cleave one strand of said newly created hemi-modified restriction endonuclease recognition site and thereby form a new extendible 3' terminus and permit the release of said single-stranded polynucleotide containing said target polynucleotide region; and (e) said primer to hybridize to said released single-stranded polynucleotide and to be extended by said polymerase and said nucleotides in a template-dependent extension to thereby form an additional copy of said linear double-stranded nucleic acid molecule;

(B) permitting: said recombinase-directed circularization (A)(iv)(a) of said linear molecule, said creation of said extendible 3' terminus (A)(iv)(b), said template dependent extension (A)(iv)(c), said restriction endonuclease cleavage (A)(iv)(d), and said primer hybridization (A)(iv)(e), to occur, thereby amplifying said target polynucleotide region of said double-stranded nucleic acid molecule; and (C) maintaining said incubation conditions until a desired level of amplification of said target polynucleotide region of said double-stranded nucleic acid molecule has been attained.

2. A method for amplifying a target polynucleotide region of a double-stranded nucleic acid molecule present in a sample, which comprises the steps:

(A) incubating linear double-stranded nucleic acid molecules in the presence of a polymerase, nucleotides, a Cre recombinase, a primer and a restriction endonuclease;

wherein:

(i) each of said linear double-stranded nucleic acid molecules has two ends and comprises:

(a) a first lox site, located at a first end of said linear molecule;

(b) a second lox site, located at a second end of said linear molecule, wherein said first and said second lox sites are oriented with respect to one another so as to permit said Cre recombinase to mediate the circularization of said linear double-stranded molecules, and to thereby form double-stranded circular molecules;

(c) said target polynucleotide region, located internal to said first and second lox sites; and (d) a hemi-modified restriction site, located between said target polynucleotide region and one of said lox sites, wherein one strand of said hemi-modified restriction site of each of said linear molecules contains at least one modified nucleotide residue;

(ii) said restriction endonuclease is substantially incapable of cleaving a strand of a nucleic acid molecule that contains said modified nucleotide residue;

(iii) said primer comprises from 3' terminus to 5' terminus:

(a) a first polynucleotide region complementary to a 3' terminal portion of said target polynucleotide region;

(b) a second polynucleotide region containing at least one of said modified nucleotide residues, wherein, if said second polynucleotide region were hybridized to a complementary polynucleotide, a double-stranded polynucleotide would thereby be formed that would contain one or more restriction endonuclease cleavage sites that would be recognized by said restriction endonuclease;

(c) a third polynucleotide region, wherein, if said third polynucleotide region were hybridized to a complementary polynucleotide, a double-stranded polynucleotide would thereby be formed that would contain a lox site; and (d) a fourth polynucleotide region having a nucleotide sequence complementary to at least a portion of said third polynucleotide region, such that said third and fourth polynucleotide regions of said primer molecule are hybridizable to one another; and (iv) said incubation is conducted under conditions suitable for permitting:

(a) said Cre recombinase to circularize said linear double-stranded nucleic acid molecules and thereby form said double-stranded circular molecules;

(b) said restriction endonuclease to cleave one strand of said hemi-modified restriction endonuclease recognition site of said double-stranded circular molecule and thereby create an extendible 3' terminus;

(c) said polymerase and said nucleotides to mediate template dependent extension of said extendible 3' terminus and thereby cause displacement of a single-stranded polynucleotide containing said target polynucleotide region; said extension further resulting in the creation of a new hemi-modified restriction recognition site;

(d) said restriction endonuclease to cleave one strand of said newly created hemi-modified restriction endonuclease recognition site and thereby form a new extendible 3' terminus and permit the release of said single-stranded polynucleotide containing said target polynucleotide region; and (e) said primer to hybridize to said released single-stranded polynucleotide and to be extended by said polymerase and said nucleotides in a template-dependent extension to thereby form an additional copy of said linear double-stranded nucleic acid molecule;

(B) permitting: said Cre recombinase-directed circularization (A)(iv)(a) of said linear molecule, said creation of said extendible 3' terminus (A)(iv)(b), said template dependent extension (A)(iv)(c), said restriction endonuclease cleavage (A)(iv)(d), and said primer hybridization (A)(iv)(e), to occur, thereby amplifying said target polynucleotide region of said double-stranded nucleic acid molecule; and (C) maintaining said incubation conditions until a desired level of amplification of said target polynucleotide region of said double-stranded nucleic acid molecule has been attained.

3. The method of claim 2, wherein the linear double-stranded nucleic acid molecules recited in step (A) comprise a primer extension of first primer molecules, said first primer molecules being single-stranded nucleic acid molecules, and comprising from 3' terminus to 5' terminus:

(1) a first polynucleotide region complementary to a 3' terminal portion of said target polynucleotide region;

(2) a second polynucleotide region containing at least one modified nucleotide residue, wherein, if said second polynucleotide region were hybridized to a complementary polynucleotide, a double-stranded polynucleotide would thereby be formed that would contain one or more restriction endonuclease cleavage sites that would be recognized by a restriction endonuclease that is substantially incapable of cleaving a strand of a nucleic acid molecule that contains said modified nucleotide residue; and (3) a third polynucleotide region, wherein, if said third polynucleotide region were hybridized to a complementary polynucleotide, a double-stranded polynucleotide would thereby be formed that would contain a lox site.

4. The method of claim 2, wherein the linear double-stranded nucleic acid molecules recited in step (A) comprise a primer extension of second primer molecules, said second primer molecules being single-stranded, and comprising from 3' terminus to 5' terminus:

(1) a first polynucleotide region having the sequence of a 5' terminal portion of said target polynucleotide region; and (2) a second polynucleotide region, wherein, if said second polynucleotide region were hybridized to a complementary polynucleotide, a double-stranded polynucleotide would thereby be formed that would contain a lox site.

5. The method of claim 3, wherein said first primer molecules additionally contain a fourth polynucleotide region, said fourth polynucleotide region of said first primer molecules being located 5' to said third polynucleotide region of said first primer molecules, and having a nucleotide sequence complementary to at least a portion thereof, such that said third and fourth polynucleotide regions of said first primer molecules are hybridized to one another.

6. The method of claim 4, wherein said second primer molecules additionally contain a third polynucleotide region, said third polynucleotide region of said second primer molecules being located 5' to said second polynucleotide region of said second primer molecules, and having a nucleotide sequence complementary to at least a portion thereof, such that said second and third polynucleotide regions of said second primer molecules are hybridized to one another.

7. The method of claim 3 wherein the linear double-stranded nucleic acid molecules recited in step (A) additionally comprise a primer extension of second primer molecules, said second primer molecules being single-stranded, and comprising from 3' terminus to 5' terminus:

(1) a first polynucleotide region having the sequence of a 5' terminal portion of said target polynucleotide; and (2) a second polynucleotide region, wherein, if said second polynucleotide region were hybridized to a complementary polynucleotide, a double-stranded polynucleotide would thereby be formed that would contain a lox site.

8. The method of claim 7, wherein said first primer molecules additionally contain a fourth polynucleotide region, said fourth polynucleotide region of said first primer molecules being located 5' to said third polynucleotide region of said first primer molecules, and having a nucleotide sequence complementary to at least a portion thereof, such that said third and fourth polynucleotide regions of said first primer molecules are hybridized to one another.

9. The method of claim 7, wherein said second primer molecules additionally contain a third polynucleotide region, said third polynucleotide region of said second primer molecules being located 5' to said second polynucleotide region of said second primer molecules, and having a nucleotide sequence complementary to at least a portion thereof, such that said second and third polynucleotide regions of said second primer molecules are hybridized to one another.

10. A method for amplifying a target polynucleotide region of a double-stranded nucleic acid molecule present in a sample, said method comprising:

(A) incubating said sample under conditions sufficient to separate the strands of said double-stranded molecule and thereby form single-stranded nucleic acid molecules;

(B) incubating said formed single-stranded nucleic acid molecules in the presence of first primer molecules, said first primer molecules being single-stranded nucleic acid molecules, and comprising from 3' terminus to 5' terminus:

(1) a first polynucleotide region complementary to a 3' terminal portion of said target polynucleotide region;

(2) a second polynucleotide region containing at least one modified nucleotide residue, wherein, if said second polynucleotide region were hybridized to a complementary polynucleotide, a double-stranded polynucleotide would thereby be formed that would contain one or more restriction endonuclease cleavage sites that would be recognized by a restriction endonuclease that is substantially incapable of cleaving a strand of a nucleic acid molecule that contains said modified nucleotide residue;

(3) a third polynucleotide region, wherein, if said third polynucleotide region were hybridized to a complementary polynucleotide, a double-stranded polynucleotide would thereby be formed that would contain a lox site; and (4) a fourth polynucleotide region having a nucleotide sequence complementary to at least a portion of said third polynucleotide region of said first primer, such that said third and fourth polynucleotide regions of said first primer molecules are hybridizable to one another; and wherein said incubation is conducted in the presence of a polymerase and nucleotides lacking the modification of the modified nucleotide residue of said first primer, said incubation being under conditions sufficient to (i) permit said first polynucleotide region of said first primer molecules to hybridize to the 3' terminus of said target polynucleotide, and (ii) permit template dependent extension of said first primer molecules, to thereby form first primer extension products;

(C) incubating said first primer extension products under conditions sufficient to separate the strands of double-stranded nucleic acid molecules and thereby produce unhybridized first primer extension products;

(D) incubating said unhybridized first primer extension products in the presence of second primer molecules, said second primer molecules being single-stranded nucleic acid molecules, and comprising from 3' terminus to 5' terminus:

(1) a first polynucleotide region having the sequence of a 5' terminal portion of said target polynucleotide; and (2) a second polynucleotide region, wherein, if said second polynucleotide region were hybridized to a complementary polynucleotide, a double-stranded polynucleotide would thereby be formed that would contain a lox site;

wherein said incubation is conducted in the presence of a polymerase and nucleotides lacking the modification of the modified nucleotides present in said first primer, said incubation being under conditions sufficient to permit (i) said unhybridized first primer extension products to hybridize to the 3' terminus of said second primer molecules, and (ii) template dependent extension of said first primer extension products, and of said second primer molecules, to thereby form linear double-stranded nucleic acid molecules having a lox site at each end, and containing said target polynucleotide that is to be amplified and a hemi-modified restriction site;

(E) incubating the linear double-stranded nucleic acid molecules of step (D) in the presence of Cre recombinase, said restriction endonuclease, said polymerase and said nucleotides lacking the modification of the modified nucleotide residue of said first primer; wherein said incubation permits the following reactions to occur:

(1) said Cre recombinase to circularize said linear double-stranded nucleic acid molecules having a lox site at each end, to thereby form a double-stranded circular molecule;

(2) said restriction endonuclease to cleave a non-modified nucleotide-containing strand of said hemi-modified restriction endonuclease recognition site of said double-stranded circular molecule to thereby form an extendible 3' terminus;

(3) said polymerase and said non-modified nucleotides to mediate template-dependent primer extension of said extendible 3' terminus to thereby cause displacement of a single-stranded polynucleotide containing said target polynucleotide region; said primer extension further resulting in the creation of a new hemi-modified restriction recognition site; and (4) said restriction endonuclease to cleave a non-modified nucleotide-containing strand of said newly created hemi-modified restriction endonuclease recognition site to thereby form a new extendible 3' terminus, and permit the release of said single-stranded polynucleotide containing said target polynucleotide region, wherein said displacement and said release accomplishes an amplification of said target polynucleotide; and (F) maintaining said incubation conditions of step (E) until a desired level of amplification of said target polynucleotide has been attained.

11. The method of claim 10, wherein said step (E) additionally permits the following reactions to occur:

(5) said first primer molecules hybridize to a 3' terminal portion of said displaced and released single-stranded polynucleotides; and (6) said polymerase and said non-modified nucleotides mediate the template-dependent extension of said hybridized first primer molecules, and of said hybridized displaced and released single-stranded polynucleotides, to thereby form linear double-stranded nucleic acid molecules having a lox site at each end, and containing said target polynucleotide region and a hemi-modified restriction site; said formed linear double-stranded molecules being substrates for said reaction (E)(1); and wherein said linear double-stranded nucleic acid molecules are permitted to become substrates of said reaction (E)(1).

12. The method of claim 10, wherein said step (E) additionally permits the following reactions to occur:

(5) said first primer molecules to hybridize to the 3' terminus of said displaced and released single-stranded polynucleotides;

(6) said polymerase and said non-modified nucleotides to mediate the template dependent extension of said hybridized first primer molecules, and of said hybridized displaced and released single-stranded polynucleotides, to thereby form linear double-stranded nucleic acid molecules having a lox site at each end, and containing said target polynucleotide region and a hemi-modified restriction site; said formed linear double-stranded molecules being substrates for said reaction (E)(1); and (7) said Cre recombinase of reaction (E)(1) to circularize said formed linear double-stranded molecules, and the circularized products of said reaction to become substrates of reactions (E)(2), (E)(3), and (E)(4).

13. The method of claim 12, wherein the conditions of incubation are maintained to permit multiple rounds of progression of reactants through the reactions of step (E).

14. The method of claim 10, wherein said second primer molecules additionally contain a third polynucleotide region, said third polynucleotide region of said second primer molecules being located 5' to said second polynucleotide region of said second primer molecules, and having a nucleotide sequence complementary to at least a portion therof, such that said second and third polynucleotide regions of said second primer molecules are hybridized to one another.

15. The method of claim 14, wherein said step (E) additionally permits the following reactions to occur:

(5) said first primer molecules to hybridize to the 3' terminus of said displaced and released single-stranded polynucleotides; and (6) said polymerase and said non-modified nucleotides to mediate the template-dependent extension of said hybridized first primer molecules, and of said hybridized displaced and released single-stranded polynucleotides, to thereby form linear double-stranded nucleic acid molecules having a lox site at each end, and containing said target polynucleotide region and a hemi-modified restriction site; said formed linear double-stranded molecules being substrates for said reaction (E)(1); and wherein said linear double-stranded nucleic acid molecules are permitted to become substrates of said reaction (E)(1).

16. The method of claim 14, wherein said step (E) additionally permits the following reactions to occur:
(5) said first primer molecules to hybridize to the 3' terminus of said displaced and released single-stranded polynucleotides;
(6) said polymerase and said non-modified nucleotides to mediate the template dependent extension of said hybridized first primer molecules, and of said hybridized displaced and released single-stranded polynucleotides, to thereby form linear double-stranded nucleic acid molecules having a lox site at each end, and containing said target polynucleotide region and a hemi-modified restriction site; said formed linear double-stranded molecules being substrates for said reaction (E)(1); and
(7) said Cre recombinase of reaction (E)(1) to circularize said formed linear double-stranded molecules, and the circularized products of said reaction to become substrates of reactions (E)(2), (E)(3), and (E)(4).

17. The method of claim 2, wherein said modified nucleotide residue is a methylated nucleotide residue.

18. The method of claim 2, wherein said modified nucleotide residue is a (a-thio)phosphorothioate nucleotide residue.

19. The method of claim 2, wherein said first primer is provided in limiting amounts, such that said method amplifies one strand of said double-stranded nucleic acid target molecule to a greater extent than the other strand.

20. A method for amplifying a target polynucleotide region of a double-stranded nucleic acid molecule present in a sample, said method comprising:
(A) incubating said sample under conditions sufficient to separate the strands of said double-stranded molecule and thereby form single-stranded nucleic acid molecules;
(B) incubating said formed single-stranded nucleic acid molecules in the presence of first primer molecules, said first primer molecules being single-stranded nucleic acid molecules, and comprising from 3' terminus to 5' terminus:
(1) a first polynucleotide region complementary to a 3' terminal portion of said target polynucleotide region;
(2) a second polynucleotide region containing at least one modified nucleotide residue, wherein, if said second polynucleotide region were hybridized to a complementary polynucleotide, a double-stranded polynucleotide would thereby be formed that would contain one or more restriction endonuclease cleavage sites that would be recognized by a restriction endonuclease that is substantially incapable of cleaving a strand of a nucleic acid molecule that contains said modified nucleotide residue; and
(3) a third polynucleotide region, wherein, if said third polynucleotide region were hybridized to a complementary polynucleotide, a double-stranded polynucleotide would thereby be formed that would contain a lox site;
wherein said incubation is conducted in the presence of a polymerase and nucleotides lacking the modification of the modified nucleotide residue of said first primer, said incubation being under conditions sufficient to (i) permit said first polynucleotide region of said first primer molecules to hybridize to the 3' terminus of said target polynucleotide, and (ii) permit template dependent extension of said first primer molecules, to thereby form first primer extension products;
(C) incubating said first primer extension products under conditions sufficient to separate the strands of double-stranded nucleic acid molecules and thereby produce unhybridized first primer extension products;
(D) incubating said unhybridized first primer extension products in the presence of second primer molecules, said second primer molecules being single-stranded nucleic acid molecules, and comprising from 3' terminus to 5' terminus:
(1) a first polynucleotide region having the sequence of a 5' terminal portion of said target polynucleotide;
(2) a second polynucleotide region, wherein, if said second polynucleotide region were hybridized to a complementary polynucleotide, a double-stranded polynucleotide would thereby be formed that would contain a lox site; and
(3) a third polynucleotide region having a nucleotide sequence complementary to at least a portion of said second polynucleotide region, such that said second and third polynucleotide regions of said second primer molecules are hybridizable to one another; and wherein said incubation is conducted in the presence of a polymerase and nucleotides lacking the modification of the modified nucleotides present in said first primer, said incubation being under conditions sufficient to permit (i)said unhybridized first primer extension products to hybridize to the 3' terminus of said second primer molecules, and (ii) template dependent extension of said first primer extension products, and of said second primer molecules, to thereby form linear double-stranded nucleic acid molecules having a lox site at each end, and containing said target polynucleotide that is to be amplified and a hemi-modified restriction site;
(E) incubating the linear double-stranded nucleic acid molecules of step (D) in the presence of Cre recombinase, said restriction endonuclease, said polymerase and said nucleotides lacking the modification of the modified nucleotide residue of said first primer; wherein said incubation permits the following reactions to occur:
(1) said Cre recombinase to circularize said linear double-stranded nucleic acid molecules having a lox site at each end, to thereby form a double-stranded circular molecule;
(2) said restriction endonuclease to cleave a non-modified nucleotide-containing strand of said hemi-modified restriction endonuclease recognition site of said double-stranded circular molecule to thereby form an extendible 3' terminus;
(3) said polymerase and said non-modified nucleotides to mediate template-dependent primer extension of said extendible 3' terminus to thereby cause displacement of a single-stranded polynucleotide containing said target polynucleotide region; said primer extension further resulting in the creation of a new hemi-modified restriction recognition site; and
(4) said restriction endonuclease to cleave a non-modified nucleotide-containing strand of said newly created hemi-modified restriction endonuclease recognition site to thereby form a new extendible 3' terminus, and permit the release of said single-stranded polynucleotide containing said target polynucleotide region, wherein said displacement and said release accomplishes an amplification of said target polynucleotide; and (F) maintaining said incubation conditions of step (E) until a desired level of amplification of said target polynucleotide has been attained.

* * * * *